(12) United States Patent  
Pitts et al.

(10) Patent No.: US 7,105,667 B2
(45) Date of Patent: Sep. 12, 2006

(54) FUSED HETEROCYCLIC COMPOUNDS AND USE THEREOF

(75) Inventors: William J. Pitts, Newtown, PA (US); Joseph Barbosa, Lambertville, NJ (US); Junqing Guo, Princeton, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 443 days.

(21) Appl. No.: 10/288,980

(22) Filed: Nov. 6, 2002

(65) Prior Publication Data

US 2003/0191143 A1    Oct. 9, 2003

Related U.S. Application Data

(63) Continuation-in-part of application No. 10/137,508, filed on May 1, 2002, now abandoned.

(60) Provisional application No. 60/368,752, filed on Mar. 29, 2002, provisional application No. 60/299,287, filed on Jun. 19, 2001, provisional application No. 60/287,964, filed on May 1, 2001.

(51) Int. Cl.
C07D 487/04 (2006.01)
C07D 471/04 (2006.01)

(52) U.S. Cl. ............ 544/279; 544/280; 540/476; 540/578

(58) Field of Classification Search ........ 514/183, 514/215, 264.11, 265.1; 540/476, 578; 544/279, 544/280

See application file for complete search history.

(56) References Cited

U.S. PATENT DOCUMENTS 3,186,991 A    6/1965  Ohnacker et al.
3,248,395 A    4/1966  Ohnacker et al.
4,973,690 A    11/1990 Rempfler et al.
5,330,989 A    7/1994  Soll et al.
5,405,848 A    4/1995  Sanfilippo et al.
6,653,300 B1*  11/2003 Bebbington et al. ........ 514/183

FOREIGN PATENT DOCUMENTS

GB         1033384         6/1966
WO      WO 99/61444      12/1999
WO      WO 01/13953       3/2001
WO      WO 01/55148       8/2001

OTHER PUBLICATIONS

Anonymous, Expert Opin Ther. Patents, 12(4), 601-603, 2002.*
Castro A, Jerez MJ, Gil C, Martinez A., Med Res Rev. pp. 229-244, Oct. 28, 2004.*
West, Anthony R., Solid State Chemistry and its Applications, Wiley, New York, 1988, pp. 358 & 365.*
Wolff, Manfred E. "Burger's Medicinal Chemistry, 5ed, Part I", John Wiley & Sons, 1995, pp. 975-977.*
Nakata A., et al., Clin. Exp. Immunol. 2002, vol. 128, pp. 460-466.

* cited by examiner

*Primary Examiner*—Thomas C. McKenzie
(74) *Attorney, Agent, or Firm*—Laurelee A. Duncan

(57) ABSTRACT

Fused heterocylic compounds of the following Formula

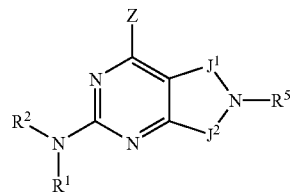

wherein $R^1$, $R^2$, $R^5$, Z, $J^1$ and $J^2$ are described herein which are useful in treating leukocyte activation-associated disorders.

6 Claims, No Drawings

FUSED HETEROCYCLIC COMPOUNDS AND USE THEREOF

This application is a continuation in part of U.S. application Ser. No. 10/137,508, filed May 1, 2002 now abandoned which claims priority to U.S. Provisional Application Ser. Nos. 60/287,964, 60/299,287 and 60/368,752, filed May 1, 2001, Jun. 19, 2001, and Mar. 29, 2002, respectively. The entirety of each of these applications is incorporated herein by reference.

FIELD OF THE INVENTION

The present invention relates to fused heterocylic compounds, pharmaceutical compositions containing these compounds, and the use of these compounds in the treatment of leukocyte activation-associated disorders.

BACKGROUND OF THE INVENTION

The immune system plays an important role in host defense. In the treatment of leukocyte activation-associated disorders is often desirable to attenuate the immune response. Such disorders include the immune response incurred by transplantation or diseases improved by decreased T-cell activation and proliferation. It is accepted that agents that inhibit T-cell proliferation may be useful in the treatment of the aforementioned disorders.

A number of agents demonstrate clinical or therapeutic utility by attenuating or modulating the immune system. Such agents include Cyclosporin A ("CsA"), azathioprine, tacrolimus, sirolimus and mycophenolate mofetil. However, these agents often demonstrate a relatively high incidence (25 to >50%) of multiple unique liabilities during clinical or therapeutic use. For example, CsA therapy is associated with nephrotoxicity, azathioprine therapy is associated with leukopenia, and tacrolimus therapy is associated with undesirable effects on the central nervous system. Also, sirolimus therapy is associated with hypertension, hyperlipidemia and hypercholesterolemia, and mycophenolate mofetil therapy is associated with diarrhea.

The overproduction of cytokines, such as TNF-α, is also implicated in a wide variety of leukocyte activation-associated disorders, including rheumatoid arthritis (RA), psoriasis, multiple sclerosis, inflammatory bowel disease, endotoxin shock, osteoporosis, Alzheimer's disease and congestive heart failure, among others. See e.g., Henry et al., *Drugs Fut.*, 24:1345–1354 (1999); Salituro et al., *Curr. Med. Chem.*, 6:807–823 (1999). There is convincing evidence in human patients that cytokine protein antagonists can provide treatment for these disorders. See e.g., Rankin et al., *Br. J. Rheumatol.*, 34:334–342 (1995) (monoclonal antibody to TNF-α—Enbrel®); and Moreland et al., *Ann. Intern. Med.*, 130:478–486 (1999) (soluble TNF-α receptor-Fc fusion protein—etanercept). Accordingly, it is accepted that agents demonstrating TNF-α inhibitory activity are useful for the treatment of leukocyte activation-associated disorders.

As none of the current treatments provide complete relief of symptoms and are often associated with various liabilities, new agents and improved methods for treating leukocyte activation-associated disorders are needed.

SUMMARY OF THE INVENTION

The present invention provides novel fused heterocyclic compounds of formula (I), their enantiomers, diastereomers, and pharmaceutically acceptable salts, prodrugs and solvates thereof, for use in treating leukocyte activation-associated disorders:

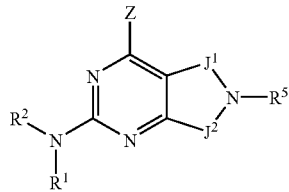

(I)

wherein:
$R^1$ is hydrogen or alkyl;
$R^2$ is
  (a) heteroaryl or heterocyclo, either of which may be optionally substituted with one to three groups $T^1$, $T^2$ and/or $T^3$;
  (b) aryl substituted with one to three groups $T^1$, $T^2$ and/or $T^3$ provided that at least one of $T^1$, $T^2$, and/or $T^3$ is other than H; or
  (c) aryl fused to a heteroaryl or heterocyclo ring wherein the combined ring system may be optionally substituted with one to three groups $T^1$, $T^2$ and/or $T^3$;
Z is $NR^3R^4$, $NR^3SO_2R^{4a}$, $OR^4$, $SR^4$, haloalkyl or halogen;
$R^3$ and $R^4$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl any of which may be optionally independently substituted where valance allows with one to three groups $T^{1a}$, $T^{2a}$ and/or $T^{3a}$;
or $R^3$ and $R^4$ may be taken together with the nitrogen atom to which they are attached to form a heterocyclo or heteroaryl ring optionally independently substituted where valance allows with one to three groups $T^{1a}$, $T^{2a}$ and/or $T^{3a}$;
$R^{4a}$ is alkyl, alkenyl, aryl, (aryl)alkyl, heteroaryl, (heteroaryl)alkyl, cycloalkyl, to (cycloalkyl)alkyl, heterocyclo or (heterocyclo)alkyl any of which may be optionally independently substituted where valance allows with one to three groups $T^{1a}$, $T^{2a}$ and/or $T^{3a}$;
$R^{3b}$ and $R^{4b}$ are independently H, alkyl, alkenyl, aryl, (aryl)alkyl, heteroaryl, (heteroaryl)alkyl, cycloalkyl, (cycloalkyl)alkyl, heterocyclo or (heterocyclo)alkyl;
$R^5$ is
  (a) hydrogen or cyano;
  (b) alkyl, alkenyl, alkynyl, cycloalkyl, (cycloalkyl)alkyl, aryl, (aryl)alkyl, heterocyclo, (heterocyclo)alkyl, heteroaryl or (heteroaryl)alkyl, any of which may be optionally independently substituted where valance allows with one to three groups $T^{1b}$, $T^{2b}$ and/or $T^{3b}$; or
  (c) $-C(O)R^6$, $-C(O)OR^6$, $-C(O)-C(O)OR^6$ or $-SO_2R^{6a}$;
$R^6$ is H, alkyl, alkenyl, $-NR^{3b}R^{4b}$, heterocyclo, (heterocyclo)alkyl, (hydroxy)alkyl, (alkoxy)alkyl, (aryloxy)alkyl, $(NR^{3b}R^{4b})$alkyl, heteroaryl, aryl or (aryl)alkyl, any of which may be optionally independently substituted where valance allows with one to three groups $T^{1b}$, $T^{2b}$ and/or $T^{3b}$;
$R^{6a}$ is alkyl, alkenyl, $-NR^{3b}R^{4b}$, heterocyclo, (heterocyclo)alkyl, (hydroxy)alkyl, (alkoxy)alkyl, (aryloxy)alkyl, $(NR^{3b}R^{4b})$alkyl, heteroaryl, aryl or (aryl)alkyl, any of which may be optionally independently substituted where valance allows with one to three groups $T^{1b}$, $T^{2b}$ and/or $T^{3b}$;
$J^1$ and $J^2$ are independently optionally substituted $C_{1-3}$ alkylene, provided that $J^1$ and $J^2$ are not both greater than $C_2$ alkylene;

$T^{1-1b}$, $T^{2-2b}$, and $T^{3-3b}$ are each independently
  (1) hydrogen or $T^6$, where $T^6$ is
    (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
    (ii) a group (i) which is itself substituted by one or more of the same or different groups (i); or
    (iii) a group (i) or (ii) which is independently substituted by one or more (preferably 1 to 3) of the following groups (2) to (13) of the definition of $T^{1-1b}$, $T^{2-2b}$ and $T^{3-3b}$;
  (2) —OH or —$OT^6$;
  (3) —SH or —$ST^6$;
  (4) —$C(O)_tH$, —$C(O)_tT^6$, or —O—$C(O)T^6$, where t is 1 or 2;
  (5) —$SO_3H$, —$S(O)_tT^6$, or $S(O)_tN(T^9)T^6$;
  (6) halo;
  (7) cyano;
  (8) nitro;
  (9) -$T^4$-$NT^7T^8$;
  (10) -$T^4$-$N(T^9)$-$T^5$-$NT^7T^8$;
  (11) -$T^4$-$N(T^{10})$-$T^5$-$T^6$;
  (12) -$T^4$-$N(T^{10})$-$T^5$-H; or
  (13) oxo;
$T^4$ and $T^5$ are each independently
  (1) a single bond;
  (2) -$T^{11}$-$S(O)_t$-$T^{12}$-;
  (3) -$T^{11}$-$C(O)$-$T^{12}$-;
  (4) -$T^{11}$-$C(S)$-$T^{12}$-;
  (5) -$T^{11}$-O-$T^{12}$-;
  (6) -$T^{11}$-S-$T^{12}$-;
  (7) -$T^{11}$-O—$C(O)$-$T^{12}$-;
  (8) -$T^{11}$-$C(O)$—O-$T^{12}$-;
  (9) -$T^{11}$-$C(=NT^{9a})$-$T^{12}$-; or
  (10) -$T^{11}$-$C(O)$—$C(O)$-$T^{12}$-;
$T^7$, $T^8$, $T^9$, $T^{9a}$ and $T^{10}$
  (1) are each independently hydrogen or a group provided in the definition of $T^6$;
  (2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^{1-1b}$, $T^{2-2b}$ and/or $T^{3-3b}$;
  (3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the description of $T^{1-1b}$, $T^{2-2b}$ and/or $T^{3-3b}$; or
  (4) $T^7$ and $T^8$ or $T^9$ and $T^{10}$ together with the nitrogen atom to which they are attached may combine to form a group —N=$CT^{13}T^{14}$ where $T^{13}$ and $T^{14}$ are each independently H or a group provided in the definition of $T^6$; and
$T^{11}$ and $T^{12}$ are each independently
  (1) a single bond;
  (2) alkylene;
  (3) alkenylene; or
  (4) alkynylene.

Preferred compounds within the scope of the present invention include compounds of Formula (I), and pharmaceutically acceptable salts, prodrugs and solvates thereof, in which the substituents $R^1$, $R^2$, Z, $J^1$, $J^2$ and $R^5$ are selected from the following:
$R^1$ is H;
$R^2$ is
  (a) heteroaryl (preferably thiazolyl, oxazolyl or isoxazolyl) optionally substituted with one to three groups $T^1$, $T^2$ and/or $T^3$ (preferably H, alkyl, haloalkyl, halo, heteroaryl, $C(O)_tT^6$, $OT^6$ or -$T^4NT^7T^8$);
  (b) aryl substituted with one to three groups $T^1$, $T^2$ and/or $T^3$ (preferably heteroaryl [more preferably, imidazolyl, oxazolyl, or thiazolyl, any of which may be further optionally substituted], cyano, $C(O)_tT^6$, $S(O)_tN(T^9)T^6$, halo alkyl, and/or haloalkyl); or
  (c) aryl fused to a heterocyclo ring (preferably, tetrahydro indole bound through the aryl ring, quinolyl bound through the aryl ring [especially quinol-6-yl], quinazolinyl bound through the aryl ring [especially quinazolin-7-yl], cinnolinyl bound through the aryl ring [especially cinnolin-6-yl], isoqinolinyl bound through the aryl ring [especially isoquinol-6-yl], and phthalazinyl bound through the aryl ring [especially phthalazin-6-yl]) wherein the combined ring system may be optionally substituted with one to three groups $T^1$, $T^2$ and/or $T^3$ [especially halo, OH, $OT^6$, alkyl, —$CO_tH$, —$CO_tT^6$ and/or —$C(O)NT^7T^8$];
Z is —$NR^3R^4$ or $OR^4$;
$R^3$ is H, alkyl or cycloalkyl;
$R^4$ is alkyl optionally independently substituted with one to three groups $T^{1a}$, $T^{2a}$ and/or $T^{3a}$, or (aryl)alkyl optionally independently substituted with one to three groups $T^{1a}$, $T^{2a}$ and/or $T^{3a}$.(especially where the aryl group is independently substituted with one or more $OT^6$, $S(O)_tT^6$ and/or $S(O)_tN(T^9)T^6$);
or $R^3$ and $R^4$ may be taken together with the nitrogen atom to which they are attached to form a heterocyclo ring (preferably piperidyl, piperazinyl and morpholinyl) optionally independently substituted with one to three groups $T^{1a}$, $T^{2a}$ and/or $T^{3a}$ (especially hydroxy, oxo and/or —$C(O)_tT^6$);
$R^5$ is
  (a) hydrogen or cyano;
  (b) alkyl, alkenyl, alkynyl, cycloalkyl, (cycloalkyl)alkyl, aryl, (aryl)alkyl, heterocyclo, (heterocyclo)alkyl, heteroaryl (preferably pyridyl, furanyl, thienyl and thiazoly) or (heteroaryl)alkyl, any of which may be optionally independently substituted one to three groups $T^{1b}$, $T^{2b}$ and/or $T^{3b}$ (especially cyano, —$OT^6$, —$C(O)_tT^6$ and/or —$S(O)_tT^6$); or
  (c) —$C(O)R^6$, —$C(O)OR^6$, —$C(O)$—$C(O)OR^6$ or —$SO_2R^{6a}$;
$R^6$ is H, alkyl, alkenyl, —$NR^{3b}R^{4b}$, heterocyclo (especially including morpholinyl, piperazinyl, and tetrahydrofuranyl), (heterocyclo)alkyl, (hydroxy)alkyl, (alkoxy)alkyl, (aryloxy)alkyl, ($NR^{3b}R^{4b}$)alkyl, heteroaryl, (heteroaryl)alkyl, aryl or (aryl)alkyl, any of which may be optionally independently substituted where valance allows with one to three groups $T^{1b}$, $T^{2b}$ and/or $T^{3b}$ (especially alkyl, —$C(O)_tH$, —$C(O)_tT^6$, —$OC(O)T^6$, —OH, —$OT^6$, and/or —$S(O)_tT^6$);
$R^{6a}$ is alkyl, alkenyl, —$NR^{3b}R^{4b}$, heterocyclo (preferably morpholinyl, piperazinyl and tetrahydrofuranyl), (heterocyclo)alkyl, (hydroxy)alkyl, (alkoxy)alkyl, (aryloxy)alkyl, ($NR^{3b}R^{4b}$)alkyl, heteroaryl (preferably pyridyl, furanyl, thienyl and thiazoly), (heteroaryl)alkyl, aryl or (aryl)alkyl, any of which may be optionally independently substituted where valance allows with one to three groups $T^{1b}$, $T^{2b}$ and/or $T^{3b}$ (especially alkyl, —$C(O)_tH$, —$C(O)_tT^6$, —$OC(O)T^6$, —OH, —$OT^6$ and/or —$S(O)_tT^6$); and
$J^1$ and $J^2$ are independently optionally substituted $C_{1-3}$ alkylene, provided that $J^1$ and $J^2$ are not both greater than $C_2$ alkylene.

More preferred compounds within the scope of the present invention include compounds of Formula (I), and pharmaceutically acceptable salts, prodrugs and solvates thereof, wherein the substituents $R^1$, $R^2$, Z, $J^1$, $J^2$ and $R^5$ are selected from the following:

$R^1$ is H;

$R^2$ is
- (a) thiazolyl optionally substituted with one to three groups $T^1$, $T^2$ and/or $T^3$, (especially H, alkyl, haloalkyl, halo, heteroaryl, $C(O)_tT^6$, $OT^6$ and/or $-T^4NT^7T^8$);
- (b) phenyl substituted at the para position with an electon-donar group $T^1$ (preferably heteroaryl [especially imidazolyl, oxazolyl or thiazolyl any of which may be further optionally substituted], cyano, $C(O)_tT^6$ or $S(O)_tN(T^9)T^6$) and optionally further substituted with groups $T^2$ and $T^3$ (especially cyano, $C(O)_tT^6$, $S(O)_tN(T^9)T^6$, halo alkyl, and haloalkyl); or
- (c) aryl fused to a heterocyclo ring (preferably tetrahydro indole bound through the aryl ring, quinolyl bound through the aryl ring [especially quinol-6-yl], quinazolinyl bound through the aryl ring [especially quinazolin-7-yl], cinnolinyl bound through the aryl ring [especially cinnolin-6-yl], isoqinolinyl bound through the aryl ring [especially isoquinol-6-yl], and phthalazinyl bound through the aryl ring [especially phthalazin-6-yl]) wherein the combined ring system may be optionally substituted with one to three groups $T^1$, $T^2$, and/or $T^3$ (especially halo, OH, $OT^6$, alkyl, $-CO_tH$, $-CO_tT^6$ and/or $-C(O)NT^7T^8$);

Z is $-NR^3R^4$;

$R^3$ is H or alkyl cycloalkyl;

$R^4$ is (aryl)alkyl optionally independently substituted with one to three groups $T^{1a}$, $T^{2a}$ and/or $T^{3a}$.(especially where the aryl group is independently substituted with one or more $OT^6$, $S(O)_tT^6$ and/or $S(O)_tN(T^9)T^6$);

or $R^3$ and $R^4$ may be taken together with the nitrogen atom to which they are attached to form a heterocyclo ring (preferably piperidyl, piperazinyl and morpholinyl) optionally independently substituted with one to three groups $T^{1a}$, $T^{2a}$ and/or $T^{3a}$ (especially hydroxy, oxo and/or $-C(O)_tT^6$);

$R^5$ is
- (a) hydrogen, or cyano;
- (b) alkyl, alkenyl, (cycloalkyl)alkyl, (aryl)alkyl, or (heteroaryl)alkyl (where the heteroaryl groups include pyridyl, furanyl, thienyl, and thiazoly), any of which may be optionally independently substituted one to three groups $T^{1b}$, $T^{2b}$ and/or $T^{3b}$ (especially cyano, $-OT^6$, and $-S(O)_tT^6$); or
- (c) $-C(O)R^6$, $-C(O)OR^6$, $-C(O)-C(O)OR^6$ or $-SO_2R^{6a}$);

$R^6$ is H, alkyl, alkenyl, $-NR^{3b}R^{4b}$, heterocyclo (preferably morpholinyl, piperazinyl and tetrahydrofuranyl), (heterocyclo)alkyl, (hydroxy)alkyl, (alkoxy)alkyl, (aryloxy)alkyl, $(NR^{3b}R^{4b})$alkyl, any of which may be optionally independently substituted where valance allows with one to three groups $T^{1b}$, $T^{2b}$ and/or $T^{3b}$ (especially alkyl, $-C(O)_tH$, $-C(O)_tT^6$, $-OC(O)T^6$, $-OH$, $-OT^6$ and/or $-S(O)_tT^6$);

$R^{6a}$ is H, alkyl, alkenyl, $-NR^{3b}R^{4b}$, heterocyclo (preferably morpholinyl, piperazinyl and tetrahydrofuranyl), (heterocyclo)alkyl, (hydroxy)alkyl, (alkoxy)alkyl, (aryloxy)alkyl, $(NR^{3b}R^{4b})$alkyl, any of which may be optionally independently substituted where valance allows with one to three groups $T^{1b}$, $T^{2b}$ and/or $T^{3b}$ (especially alkyl, $-C(O)_tH$, $-C(O)_tT^6$, $-OC(O)T^6$, $-OH$, $-OT^6$ and/or $-S(O)_tT^6$); and $J^1$ and $J^2$ are independently optionally substituted $C_{1-3}$ alkylene, provided that $J^1$ and $J^2$ are not both greater than $C_2$ alkylene.

Preferred compounds of the present invention include compounds of formula (IIa) and formula (IIb)

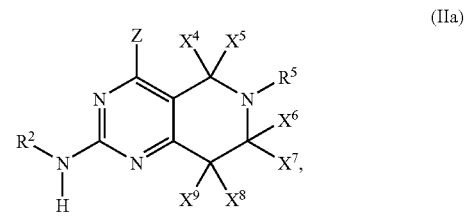
(IIa)

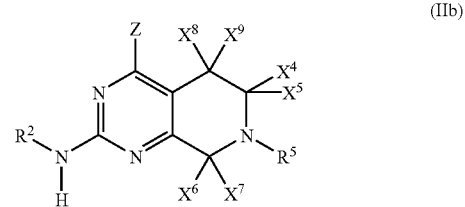
(IIb)

and pharmaceutically acceptable salts, prodrugs and solvates thereof, wherein:

$R^2$ is:

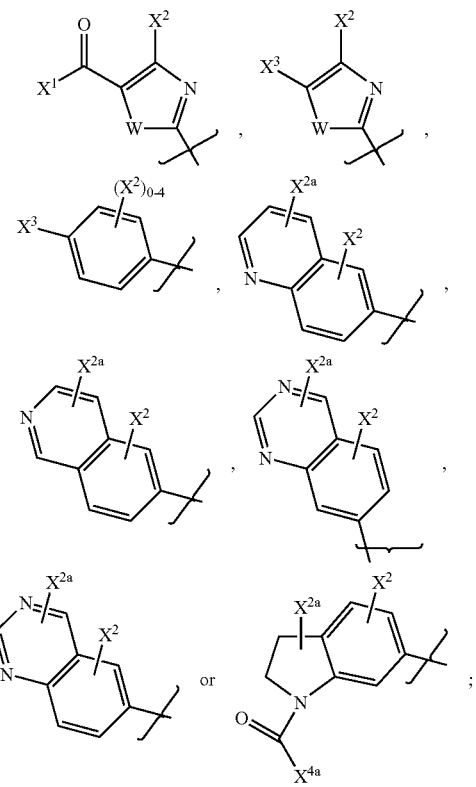

W is O or S (more preferably S);

$X^1$ $NHT^8$ or $OT^6$;

$X^2$ and $X^{2a}$ are independently hydrogen, halo, $OT^6$, alkyl or haloalkyl;

$X^3$ is heteroaryl (preferably, pyrimidinyl, imidazolyl, oxazolyl or thiazolyl, any of which may be further optionally substituted), cyano, $C(O)_tT^6$ or $S(O)_tNT^7T^8$;

$X^{4a}$ is alkyl, haloalkyl, $NHT^8$ or $OT^6$;

$X^4$, $X^5$, $X^6$ and $X^7$ are independently chosen from hydrogen, $T^6$, $OT^6$ or $NT^7T^8$, or $X^4$ and $X^5$ or $X^6$ and $X^7$ may be taken together to be a carbonyl group; and $X^8$ and $X^9$ are independently chosen from hydrogen, $T^6$, $OT^6$ or $NT^7T^8$.

Preferred compounds of the present invention include compounds of formulas (IIIa), (IIIb) and (IIIc)

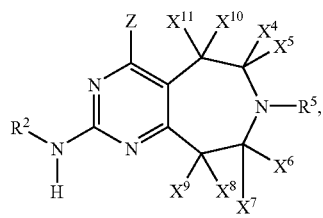
(IIIa)

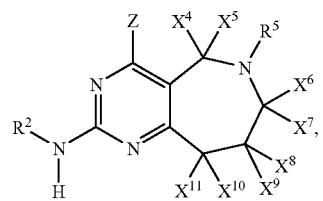
(IIIb)

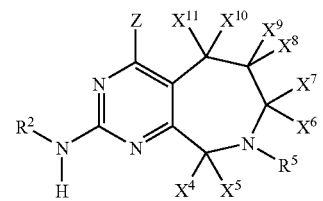
(IIIc)

and pharmaceutically acceptable salts, prodrugs and solvates thereof,
wherein:
$R^2$ is

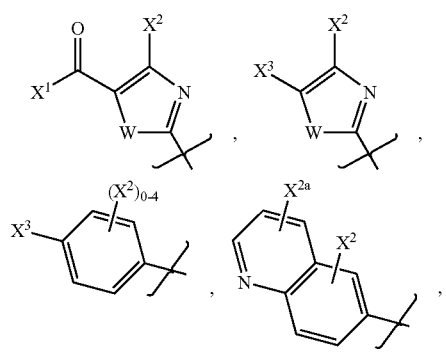

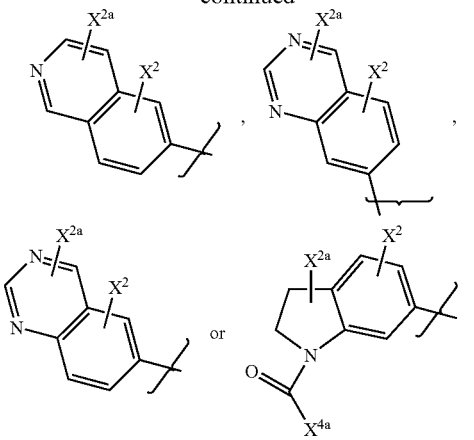
-continued

W is O or S, (more preferably S);

$X^1$ is $NHT^8$ or $OT^6$;

$X^2$ and $X^{2a}$ are independently hydrogen, halo, $OT^6$, alkyl or haloalkyl;

$X^3$ is heteroaryl (preferably, pyrimidinyl, imidazolyl, oxazolyl or thiazolyl, any of which may be further optionally substituted), cyano, $C(O)_tT^6$ or $S(O)_tNT^7T^8$;

$X^{4a}$ is alkyl, haloalkyl, $NHT^8$ or $OT^6$;

$X^4$, $X^5$, $X^6$ and $X^7$ are independently chosen from hydrogen, $T^6$, $OT^6$, or $NT^7T^8$, or $X^4$ and $X^5$, or $X^6$ and $X^7$ may be taken together to be a carbonyl group; and $X^8$ $X^9$ $X^{10}$ and $X^{11}$ are independently chosen from hydrogen, $T^6$, $OT^6$, or $NT^7T^8$.

Preferred compounds of the present invention include compounds of formula (IV),

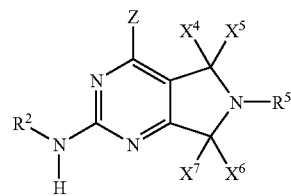
(IV)

and pharmaceutically acceptable salts, prodrugs and solvates thereof,
wherein:
$R^2$ is

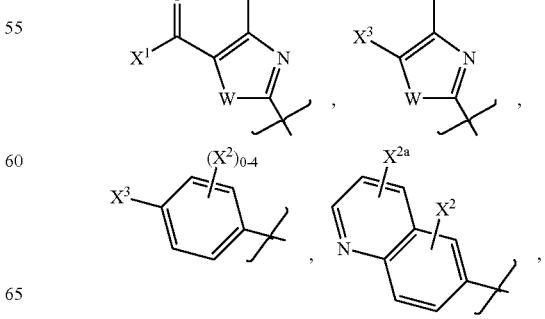

-continued

W is O or S (more preferably S);
X$^1$ is NHT$^8$ or OT$^6$;
X$^2$ and X$^{2a}$ are independently hydrogen, halo, OT$^6$, alkyl or haloalkyl;
X$^3$ is heteroaryl (preferably, pyrimidinyl, imidazolyl, oxazolyl or thiazolyl, any of which may be further optionally substituted), cyano, C(O)$_t$T$^6$ or S(O)$_t$NT$^7$T$^8$;
X$^{4a}$ is alkyl, haloalkyl, NHT$^8$ or OT$^6$; and
X$^4$, X$^5$, X$^6$ and X$^7$ are independently chosen from hydrogen, T$^6$, OT$^6$, or NT$^7$T$^8$, or
X$^4$ and X$^5$ or X$^6$ and X$^7$ may be taken together to be a carbonyl group Preferred compounds include compounds of formula V (V)

and pharmaceutically acceptable salts, prodrugs and solvates thereof,
wherein:
R$^{1b}$ is H or alkyl;
R$^{2b}$ is optionally substituted heteroaryl;
R$^{3b}$ is H or alkyl;
R$^{4b}$ is optionally substituted (aryl)alkyl;
R$^{5b}$ is H, alkyl, or —C(O)—(CH$_2$)$_v$—O—Y—R$^{6b}$, where Y is a bond or —C(O)—, R$^{6b}$ is hydrogen or alkyl, and v is an integer from 0 to 2;
J$^1$ and J$^2$ are independently optionally substituted C$_{1-3}$ alkylene, provided that J$^1$ and J$^2$ are not both greater than C$_2$ alkylene;
X$^4$ and X$^5$ are optional substituents bonded to any available carbon atom in one or both of J$^1$ and J$^2$, independently selected from hydrogen, OR$^7$, —NR$^8$R$^9$, alkyl, substituted alkyl, alkenyl, substituted alkenyl, alkynyl, substituted alkynyl, cycloalkyl, substituted cycloalkyl, aryl, substituted aryl, heterocycloalkyl, or heteroaryl;
R$^7$ is hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocycloalkyl, C(O)heteroaryl, aryl, substituted aryl, heterocycloalkyl and heteroaryl; and R$^8$ and R$^9$ are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocycloalkyl, C(O)heteroaryl, S(O)$_2$alkyl, S(O)$_2$substituted alkyl, S(O)$_2$cycloalkyl, S(O)$_2$substituted cycloalkyl, S(O)$_2$aryl, S(O)$_2$ substituted aryl, S(O)$_2$heterocycloalkyl, S(O)$_2$heteroaryl, aryl, substituted aryl, heterocycloalkyl, and heteroaryl, or R$_8$ and R$_9$ taken together with the nitrogen atom to which they are attached complete an optionally substituted heterocycloalkyl or heteroaryl ring.

Preferred compounds within the scope of formula (V) include compounds of formula (Va) and (Vb), (Va)

(Vb)

and pharmaceutically acceptable salts, prodrugs and solvates thereof,
wherein:
R$^{1b}$, R$^{2b}$, R$^{3b}$, R$^{4b}$, X$^4$ and X$^5$ are as defined above;
R$^{5b1}$ is H or alkyl; and
R$^{5b2}$ is —C(O)—(CH$_2$)$_v$—O—Y—R$^{6b}$, where Y is a bond or —C(O)—, R$^{6b}$ is hydrogen or alkyl, and v is an integer from 0 to 2;

Preferred compounds within Formula V, and pharmaceutically acceptable salts, prodrugs and solvates thereof, are those wherein:
R$^{1b}$ is H;
R$^{2b}$ is thiazolyl, oxazolyl or isoxozolyl (preferably thiazolyl), any of which may be optionally substituted (preferably with one or more alkyl or alkoxycarbonyl groups);
R$^{3b}$ is H;
R$^{4b}$ is optionally substituted (pheny)alkyl, (preferably substituted with one or more group of the formula —SO$_2$R$^{8b}$ where R$^{8b}$ is alkyl, amino, alkylamino or dialkylamino);
R$^{5b}$ is alkyl, or —C(O)—(CH$_2$)$_v$—O—Y—R$^{6b}$ where Y is a bond or —C(O)—, R$^{6b}$ is hydrogen or alkyl, and v is 1;
J$^1$ is an alkylene group of 1 or 2 carbon atoms;
J$^2$ is an alkylene group of 2 carbon atoms; and
X$^4$ and X$^5$ are each H.

More preferred compounds within Formula V are those wherein $R^{1b}$ is H;

$R^{2b}$ is

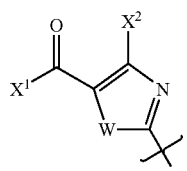

where W is O or S (preferably S), $X^1$ is alkoxy, and $X^2$ is alkyl;

$R^{3b}$ is H;

$R^{4b}$ is (pheny)alkyl substituted with one or more group of the formula —$SO_2R^{8b}$ where $R^{8b}$ is alkyl, or amino;

$R^{5b}$ is alkyl, or —C(O)—(CH$_2$)$_v$—O—Y—$R^{6b}$, where Y is a bond or —C(O)—, $R^{6b}$ is hydrogen or alkyl, and v is 1;

$J^1$ is an alkylene group of 1 or 2 carbon atoms;

$J^2$ is an alkylene group of 2 carbon atoms; and $X^4$ and $X^5$ are each H.

Preferred compounds within the scope of Formula V, include:

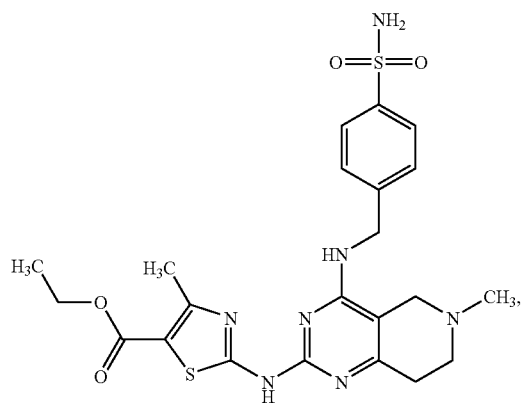

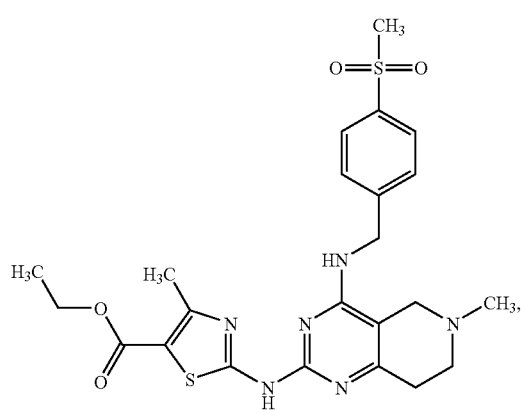

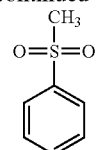

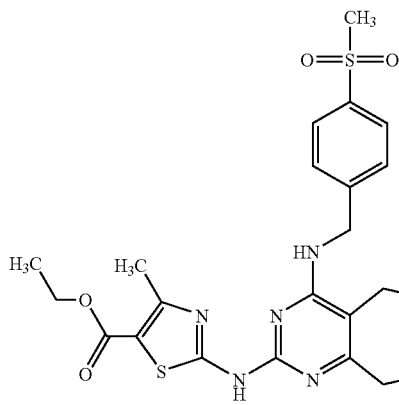

The following are definitions of the terms as used throughout this specification and claims. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, etc. Lower alkyl groups, that is, alkyl groups of 1 to 6 carbon atoms, are generally most preferred.

The term "substituted alkyl" refers to alkyl groups substituted with one or more groups listed in the definition of $T^{1-1b}$, $T^{2-2b}$ and $T^{3-3b}$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, C(O)$NR_8R_9$, C(O)alkyl and C(O)H.

The term "alkylene" refers to a straight chain bridge of 1 to 4 carbon atoms connected by single bonds (e.g., —(CH$_2$)$_x$— wherein x is 1 to 5), which may be substituted with one or more groups listed in the definition of $T^{1-1b}$, $T^{2-2b}$ and $T^{3-3b}$.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl.

The term "substituted alkenyl" refers to an alkenyl group as defined above substituted with one or more groups listed in the definition of $T^{1-1b}$, $T^{2-2b}$ and $T^{3-3b}$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, C(O)$NR_8R_9$, C(O)alkyl, and C(O)H.

The term "alkynyl" refers to straight or branched chain hydrocarbon group having 2 to 12 carbon atoms and one, two or three triple bonds, preferably 2 to 6 carbon atoms and one triple bond.

The term "substituted alkynyl" refers to an alkynyl group as defined above substituted with one or more groups listed in the definition of $T^{1-1b}$, $T^{2-2b}$ and $T^{3-3b}$, preferably selected from halo, cyano, O—$R_7$, S—$R_7$, $NR_8R_9$, nitro, cycloalkyl, substituted cycloalkyl, oxo, aryl, substituted aryl, heterocyclo, heteroaryl, $CO_2R_7$, $S(O)R_7$, $SO_2R_7$, $SO_3R_7$, $SO_2NR_8R_9$, $C(O)NR_8R_9$, C(O)alkyl, and C(O)H.

The term "halo" refers to chloro, bromo, fluoro, and iodo.

The term "cycloalkyl" refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 7 carbons, forming the ring and which may be fused to 1 or 2 aromatic or heterocyclo rings, which include cyclopropyl, cyclobutyl, cyclopentyl, cyclohexyl, cycloheptyl, cyclooctyl, cyclodecyl, cyclododecyl, cyclohexenyl,

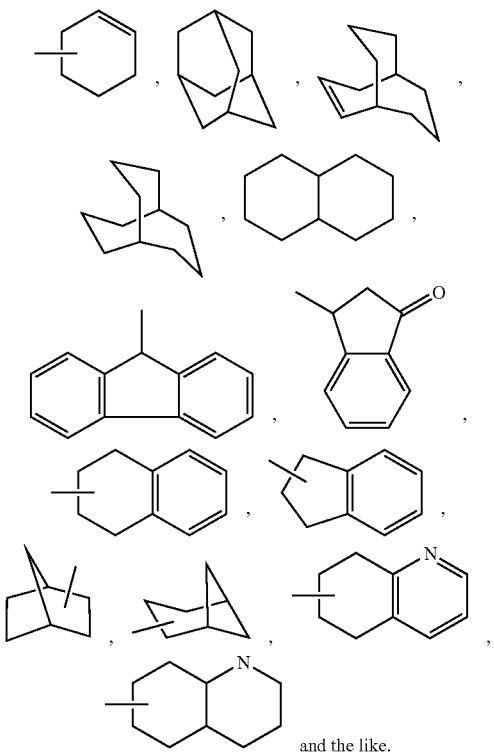

and the like.

The term "substituted cycloalkyl" refers to such cycloalkyl group as defined above substituted with one or more groups listed in the definition of $T^{1-1b}$, $T^{2-2b}$ and $T^{3-3b}$ preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})_pO$ $(CR_{14}R_{15})_qCO_2R_7$, $CO(CR_{12}R_{13})_rOR_7$, $CO(CR_{12}R_{13})_pO(CR_{14}R_{15})_qR_7$, $CO(CR_{12}R_{13})_rNR_8R_9$, $OC(O)O(CR_{12}R_{13})_mNR_8R_9$, $OC(O)N(CR_{12}R_{13})_rR_7$, $O(CR_{12}R_{13})_mNR_8R_9$, $NR_{10}C(O)(CR_{12}R_{13})_rR_7$, $NR_{10}C(O)(CR_{12}R_{13})_rOR_7$, $NR_{10}C(=NC)(CR_{12}R_{13})_rR_7$, $NR_{10}CO(CR_{12}R_{13})_rNR_8R_9$, $NR_{10(CR12}R_{13})_mOR_7$, $NR_{10}(CR_{12}R_{13})_rCO_2R_7$, $NR_{10}(CR_{12}R_{13})_mNR_8R_9$, $NR_{10}(CR_{12}R_{13})_nSO_2(CR_{14}R_{15})_qR_7$, $CONR_{10}(CR_{12}R_{13})_nSO_2(CR_{14}R_{15})_qR_7$, $SO_2NR_{10}(CR_{12}R_{13})_nCO(CR_{14}R_{15})_qR_7$, and $SO_2NR_{10}(CR_{12}R_{13})_mOR_7$.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl, as well as such rings fused to a cycloalkyl, cycloalkenyl, heterocyclo, or heteroaryl ring. Examples include:

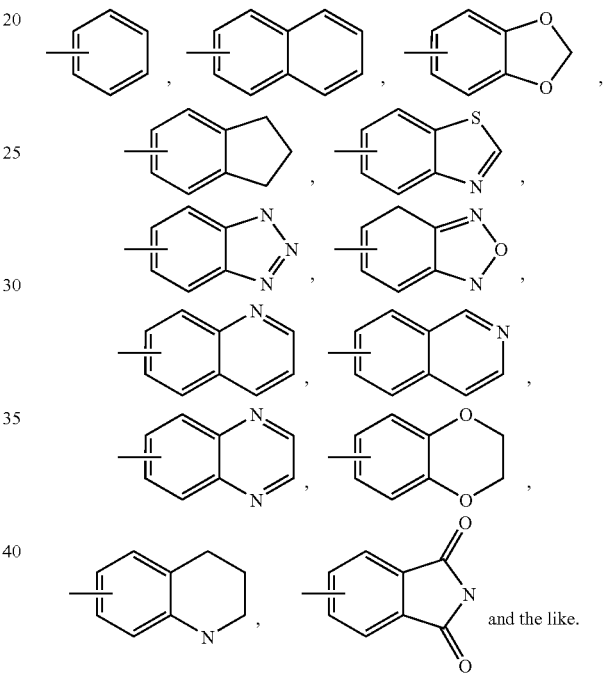

and the like.

The term "substituted aryl" refers to such aryl groups as defined above substituted with one or more groups listed in the definition of $T^{1-1b}$, $T^{2-2b}$ and $T^{3-3b}$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)$ $R_7$, $NR_8R_9$, $NR_{10}C(O)R_7$, $NR_{10}C(O)OR_7$, $NR_{10}C(O)C(O)$ $OR_7$, $NR_{10}C(O)C(O)NR_8R_9$, $NR_{10}C(O)C(O)$alkyl, $NR_{10}C$ $(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})_pO(CR_{14}R_{15})_qCO_2R_7$, $CO(CR_{12}R_{13})_rOR_7$, $CO(CR_{12}R_{13})_pO(CR_{14}R_{15})_qR_7$, $CO(CR_{12}R_{13})_rNR_8R_9$, $OC(O)O(CR_{12}R_{13})_mNR_8R_9$, $OC(O)N(CR_{12}R_{13})_rR_7$, $O(CR_{12}R_{13})_mNR_8R_9$, $NR_{10}C(O)(CR_{12}R_{13})_rR_7$, $NR_{10}C(O)$ $(CR_{12}R_{13})_rOR_7$, $NR_{10}C(=NC)(CR_{12}R_{13})_rR_7$, $NR_{10}CO$ $(CR_{12}R_{13})_rNR_8R_9$, $NR_{10}(CR_{12}R_{13})_mOR_7$, $NR_{10}(CR_{12}R_{13})_rCO_2R_7$, $NR_{10}(CR_{12}R_{13})_mNR_8R_9$, $NR_{10}(CR_{12}R_{13})_nSO_2(CR_{14}R_{15})_qR_7$, $CONR_{10}(CR_{12}R_{13})_nSO_2(CR_{14}R_{15})_qR_7$, $SO_2NR_{10}(CR_{12}R_{13})_nCO(CR_{14}R_{15})_qR_7$, and $SO_2NR_{10}(CR_{12}R_{13})_mOR_7$ as well as pentafluorophenyl.

The terms "heterocycle", "heterocyclic", "heterocyclic group" or "heterocyclo" refer to fully saturated or partially unsaturated cyclic groups (for example, 3 to 13 member monocyclic, 7 to 17 member bicyclic, or 10 to 20 member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions. Exemplary heterocyclic groups include

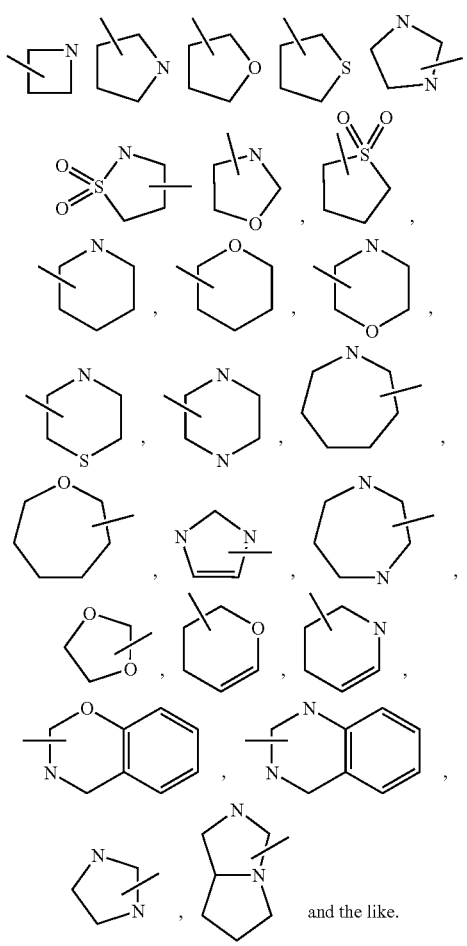

and the like.

The terms "substituted heterocycle" or "substituted heterocyclo" and the like refer to such heterocyclo groups as defined above substituted with one or more groups listed in the definition of $T^{1-1b}$, $T^{2-2b}$ and $T^{3-3b}$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)$alkyl, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})_pO(CR_{14}R_{15})_qCO_2R_7$, $CO(CR_{12}R_{13})_rOR_7$, $CO(CR_{12}R_{13})_pO(CR_{14}R_{15})_qR_7$, $CO(CR_{12}R_{13})_rNR_8R_9$, $OC(O)O(CR_{12}R_{13})_mNR_8R_9$, $OC(O)N(CR_{12}R_{13})_rR_7$, $O(CR_{12}R_{13})_mNR_8R_9$, $NR_{10}C(O)(CR_{12}R_{13})_rR_7$, $NR_{10}C(O)(CR_{12}R_{13})_rOR_7$, $NR_{10}C(=NC)(CR_{12}R_{13})_rR_7$, $NR_{10}CO(CR_{12}R_{13})_rNR_8R_9$, $NR_{10}(CR_{12}R_{13})_mOR_7$, $NR_{10}(CR_{12}R_{13})_rCO_2R_7$, $NR_{10}(CR_{12}R_{13})_mNR_8R_9$, $NR_{10}(CR_{12}R_{13})_nSO_2(CR_{14}R_{15})_qR_7$, $CONR_{10}(CR_{12}R_{13})_nSO_2(CR_{14}R_{15})_qR_7$, $SO_2NR_{10}(CR_{12}R_{13})_nCO(CR_{14}R_{15})_qR_7$, and $SO_2NR_{10}(CR_{12}R_{13})_mOR_7$.

The term "heteroaryl" as used herein alone or as part of another group refers to a 5- 6- or 7-membered aromatic rings containing from 1 to 4 nitrogen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be optionally substituted with substituents listed in the definition of $T^{1-1b}$, $T^{2-2b}$ and $T^{3-3b}$. Also an available nitrogen or sulfur atom in the heteroaryl ring can be oxidized. Examples of heteroaryl rings include,

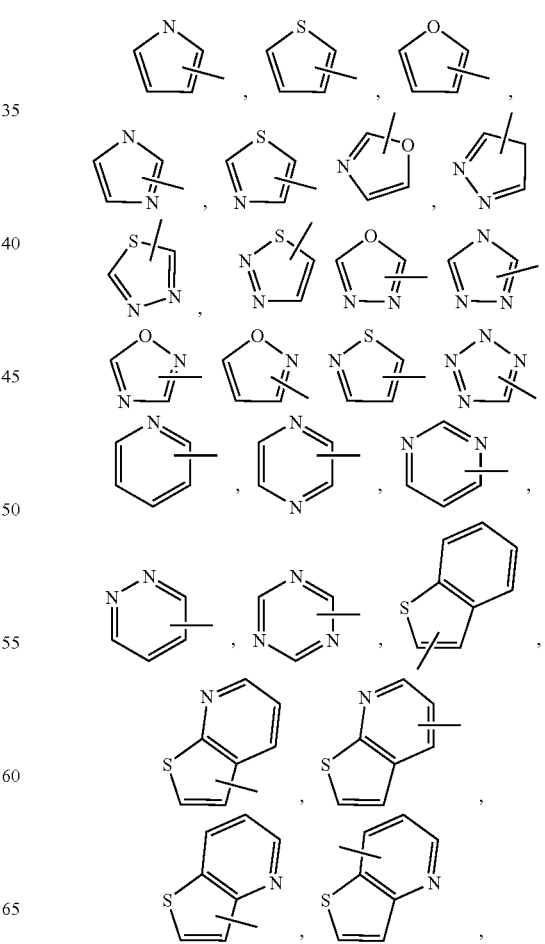

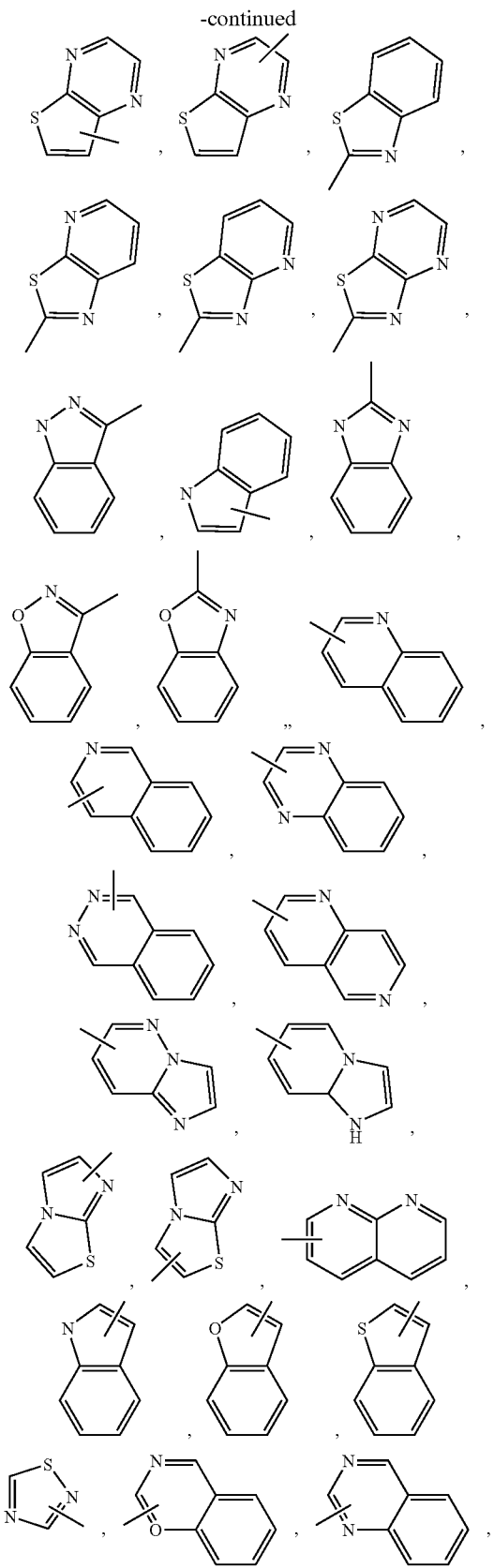

and the like.

The term "substituted heteroaryl" refers to such heteroaryl groups as defined above substituted on any available atom with one or more groups listed in the definition of $T^{1-1b}$, $T^{2-2b}$ and $T^{3-3b}$, "preferably selected from" refers to such heterocyclo groups as defined above substituted with one or more groups listed in the definition of $T^{1-1b}$, $T^{2-2b}$ and $T^{3-3b}$, preferably selected from halogen, nitro, alkyl, substituted alkyl, alkenyl, cyano, cycloalkyl, substituted cycloalkyl, aryl, substituted aryl, heterocyclo, heteroaryl, oxo, $OR_7$, $CO_2R_7$, $C(O)NR_8R_9$, $OC(O)R_7$, $OC(O)OR_7$, $OC(O)NR_8R_9$, $OCH_2CO_2R_7$, $C(O)R_7$, $NR_8R_9$, $NR_{10}C(O)R_7$, $NR_{10}C(O)OR_7$, $NR_{10}C(O)C(O)OR_7$, $NR_{10}C(O)C(O)NR_8R_9$, $NR_{10}C(O)C(O)alkyl$, $NR_{10}C(NCN)OR_7$, $NR_{10}C(O)NR_8R_9$, $NR_{10}C(NCN)NR_8R_9$, $NR_{10}C(NR_{11})NR_8R_9$, $NR_{10}SO_2NR_8R_9$, $NR_{10}SO_2R_7$, $SR_7$, $S(O)R_7$, $SO_2R_7$, $SO_3R_7$, $SO_2NR_8R_9$, $NHOR_7$, $NR_{10}NR_8R_9$, $N(COR_7)OR_{10}$, $N(CO_2R_7)OR_{10}$, $C(O)NR_{10}(CR_{12}R_{13})_rR_7$, $CO(CR_{12}R_{13})_pO(CR_{14}R_{15})_qCO_2R_7$, $CO(CR_{12}R_{13})_rOR_7$, $CO(CR_{12}R_{13})_pO(CR_{14}R_{15})_qR_7$, $CO(CR_{12}R_{13})_rNR_8R_9$, $OC(O)O(CR_{12}R_{13})_mNR_8R_9$, $OC(O)N(CR_{12}R_{13})_rR_7$, $O(CR_{12}R_{13})_mNR_8R_9$, $NR_{10}C(O)(CR_{12}R_{13})_rR_7$, $NR_{10}C(O)(CR_{12}R_{13})_rOR_7$, $NR_{10}C(=NC)(CR_{12}R_{13})_rR_7$, $NR_{10}CO(CR_{12}R_{13})_rNR_8R_9$, $NR_{10}(CR_{12}R_{13})_mOR_7$, $NR_{10}(CR_{12}R_{13})_rCO_2R_7$, $NR_{10}(CR_{12}R_{13})_mNR_8R_9$, $NR_{10}(CR_{12}R_{13})_nSO_2(CR_{14}R_{15})_qR_7$, $CONR_{10}(CR_{12}R_{13})_nSO_2(CR_{14}R_{15})_qR_7$, $SO_2NR_{10}(CR_{12}R_{13})_nCO(CR_{14}R_{15})_qR_7$, and $SO_2NR_{10}(CR_{12}R_{13})_mOR_7$.

$R_7$, $R_{10}$, and $R_{11}$, are independently selected from the group consisting of hydrogen, alkyl, substituted alkyl, alkenyl, alkynyl, cycloalkyl, substituted cycloalkyl, C(O)alkyl, C(O)substituted alkyl, C(O)cycloalkyl, C(O) substituted cycloalkyl, C(O)aryl, C(O)substituted aryl, C(O)Oalkyl, C(O)Osubstituted alkyl, C(O)heterocyclo, C(O)heteroaryl, aryl, substituted aryl, heterocyclo and heteroaryl.

$R_8$ and $R_9$ are independently selected from the group consisting of hydrogen, alkyl, substituted alkyl, cycloalkyl, substituted cycloalkyl, alkenyl, alkynyl, C(O)alkyl, C(O) substituted alkyl, C(O)cycloalkyl, C(O)substituted cycloalkyl, C(O)aryl, C(O)substituted aryl, C(O)Oalkyl, C(O)Osubstituted alkyl, C(O)heterocyclo, C(O)heteroaryl, $S(O)_2$alkyl, $S(O)_2$substituted alkyl, $S(O)_2$cycloalkyl, $S(O)_2$ substituted cycloalkyl, $S(O)_2$aryl, $S(O)_2$substituted aryl, $S(O)_2$heterocyclo, $S(O)_2$heteroaryl, aryl, substituted aryl, heterocyclo, and heteroaryl or $R_8$ and $R_9$ taken together with the nitrogen atom to which they are attached complete a heterocyclo or heteroaryl ring.

$R_{12}$ and $R_{14}$ are independently selected from hydrogen and alkyl or 1 to 4 carbons.

$R_{13}$ and $R_{15}$ are independently selected from hydrogen, alkyl of 1 to 4 carbons, and substituted alkyl or 1 to 4 carbons.

n is zero or an integer from 1 to 4.

m is an integer from 2 to 6.

p is an integer from 1 to 3.

q is zero or an integer from 1 to 3.

r is zero or an integer from 1 to 6.

$T^1$, $T^2$, and $T^3$ are are each independently (1) hydrogen or $T_6$, where $T^6$ is (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

(ii) a group (i) which is itself substituted by one or more of the same or different groups (i); or (iii) a group (i) or (ii) which is independently substituted by one or more (preferably 1 to 3) of the following groups (2) to (13) of the definition of $T^{1-1b}$, $T^{2-2b}$ and $T^{3-3b}$;
(2) —OH or —OT$^6$,
(3) —SH or —ST$^6$,
(4) —C(O)$_t$H, —C(O)$_t$T$^6$, or —O—C(O)T$^6$, where t is 1 or 2;
(5) —SO$_3$H, —S(O)$_t$T$^6$, or S(O)$_t$N(T$^9$)T$^6$,
(6) halo,
(7) cyano,
(8) nitro,
(9) -T$^4$-NT$^7$T$^8$,
(10) -T$^4$-N(T$^9$)-T$^5$-NT$^7$T$^8$,
(11) -T$^4$-N(T$^{10}$)-T$^5$-T$^6$,
(12) -T$^4$-N(T$^{10}$)-T$^5$-H,
(13) oxo, $T^4$ and $T^5$ are each independently
(1) a single bond,
(2) -T$^{11}$-S(O)$_t$-T$^{12}$-,
(3) -T$^{11}$-C(O)-T$^{12}$-,
(4) -T$^{11}$-C(S)-T$^{12}$-,
(5) -T$^{11}$-O-T$^{12}$-,
(6) -T$^{11}$-S-T$^{12}$-,
(7) -T$^{11}$-O—C(O)-T$^{12}$-,
(8) -T$^{11}$-C(O)—O-T$^{12}$-,
(9) -T$^{11}$-C(=NT$^{9a}$)-T$^{12}$-, or
(10) -T$^{11}$-C(O)—C(O)-T$^{12}$-, $T^7$, $T^8$, $T^9$, $T^{9a}$ and $T^{10}$
(1) are each independently hydrogen or a group provided in the definition of $T^6$, or
(2) $T^7$ and $T^8$ may together be alkylene or alkenylene, completing a 3- to 8-membered saturated or unsaturated ring together with the atoms to which they are attached, which ring is unsubstituted or substituted with one or more groups listed in the description of $T^{1-1b}$, $T^{2-2b}$ and $T^{3-3b}$, or
(3) $T^7$ or $T^8$, together with $T^9$, may be alkylene or alkenylene completing a 3- to 8-membered saturated or unsaturated ring together with the nitrogen atoms to which they are attached, which ring is unsubstituted or substituted with one or more groups listed in the description of $T^{1-1b}$, $T^{2-2b}$ and $T^{3-3b}$, or
(4) $T^7$ and $T^8$ or $T^9$ and $T^{10}$ together with the nitrogen atom to which they are attached may combine to form a group —N=CT$^{13}$T$^{14}$ where $T^{13}$ and $T^{14}$ are each independently H or a group provided in the definition of $T^6$; and $T^{11}$ and $T^{12}$ are each independently
(1) a single bond,
(2) alkylene,
(3) alkenylene, or
(4) alkynylene.

The term "optionally substituted" is intended to be synonymous with "unsubstituted or substituted". For example, an optionally substituted heterocycle is equivalent to an unsubstituted or substituted heterocycle.

"T-cell mediated diseases" refers to any disorder or disease state in which modulation of the activity of T-cells is implicated in a process which results in either a pathophysiological state or a process where the normal function of T-cells is intended to be suppressed for therapeutic benefit. Examples of T-cell mediated disorders include transplant rejection, graph verses host disease, and autoimmune disorders, such as rheumatoid arthritis, multiple sclerosis, juvenile diabetes, asthma, and inflammatory bowel disease, T-cell mediated hypersensitivity diseases, ischemic or reperfusion injury, and T-cell proliferative disorders. T-cell mediated diseases are included in the definition of "leukocyte activation-associated disorders" which is defined herein, infra.

The compounds of Formula (I) in accordance with the present invention are employed, typically in the form of a pharmaceutical composition including a pharmaceutically acceptable carrier for the treatment of T-cell mediated disease. The compounds employed for this purpose are typically administered in an amount from about 0.01 to 100 mg/kg/day.

The pharmaceutical compositions comprising at least one compound of Formula (I) may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of Formula (I) may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered in the form of liposomes.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound employed in the present invention may be determined by one of ordinary skill in the art, and includes exemplary dosage amounts for an adult human of from about 0.01 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to inflammatory, immunological, or respiratory cell-associated disorders.

Compounds of Formula (I) include salts, prodrugs and solvates. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety-such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds of the Formula (I) may be formed, for example, by reacting a compound I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, where the R substituents comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of Formula (I), or a salt and/or solvate thereof. Solvates of compounds of Formula (I) are preferably hydrates.

Various forms of prodrugs are well known in the art. For examples of such prodrug derivatives, see:

a) *Design of Prodrugs,* edited by H. Bundgaard, (Elsevier, 1985) and *Methods in Enzymology,* Vol. 42, p. 309–396, edited by K. Widder, et al. (Acamedic Press, 1985);

b) *A Textbook of Drug Design and Development,* edited by Krosgaard-Larsen and H. Bundgaard, Chapter 5, "Design and Application of Prodrugs," by H. Bundgaard, pp. 113–191 (1991); and c) H. Bundgaard, *Advanced Drug Delivery Reviews,* 8, 1–38 (1992), each of which is incorporated herein by reference.

Solvates (e.g. hydrates) of the compounds of Formula (I) are also with the scope of the present invention. Methods of salvation are generally known in the art.

All stereoisomers of the present compounds, such as those which may exist due to asymmetric carbons on the R substituents of the compound of Formula (I), including enantiomeric and diastereomeric forms, are within the scope of this invention. Individual stereoisomers of the compounds of the invention may, for example, be substantially free of other isomers, or may be admixed, for example, as racemates or with all other, or other selected, stereoisomers. The chiral centers of the present invention can have an S or R configuration as defined by the IUPAC 1974 Recommendations.

METHODS OF PREPARATION

Compounds of Formula I may be prepared by reference to the methods illustrated in the following Schemes A through C. As shown therein, the end product is a compound having the same structural formula as Formula I. It will be understood that any compound of Formula I may be produced by Scheme A and B by the suitable selection of appropriate substitution. Scheme C shows the preparation of amides from compounds of Formula I derived from Schemes A and B. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

Compounds within the scope of the present invention may be prepared by several methods, including the condensation of cyclic beta-keto esters with an appropriately substituted guanidine to provide compounds of Formula 1 as illustrated in synthetic Scheme A1 In this case guanidine A1 is heated with cyclic beta-keto ester A2 to produce intermediate A3. Reaction of A3 with phosphorous oxychloride provides intermediate A4. Reaction with reagent A5, which may be an amine, an alcohol, a thiol or a sulfonamide, in the presence of a suitable base provides compound A6 having a Formula IIa, IIb, IIIa, IIIb, IIIc or IV.

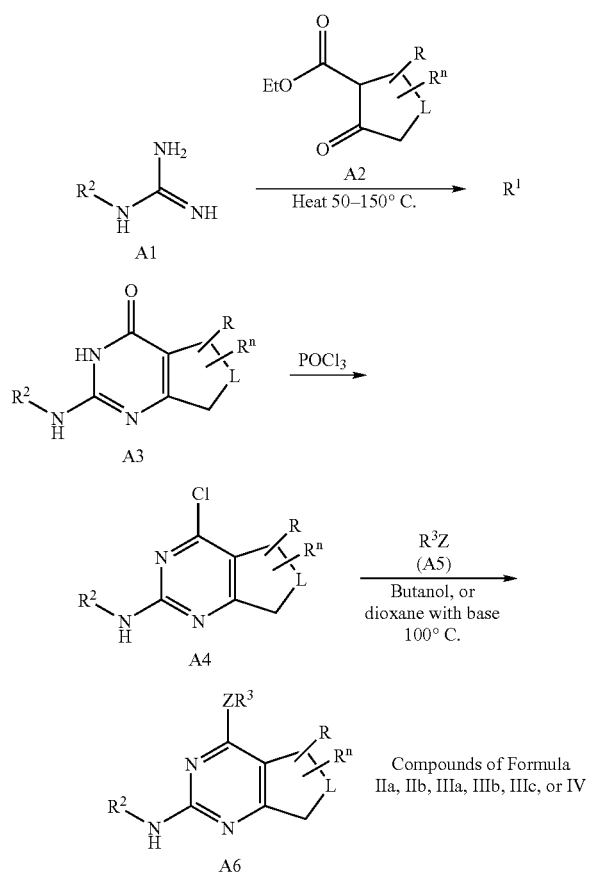

Z = —NR—, —O—, —S—, —SO$_2$NR—
R, R$^n$ = a substituent
n = an integer
L = —NR$^5$—, —NR$^5$CR$^3$R$^4$—, —CR$^3$R$^4$NR$^5$—,
  —CR$^3$R$^4$NR$^5$CR$^3$R$^4$—, —NR$^5$CR$^3$R$^4$CR$^3$R$^4$—, or
  —CR$^3$R$^4$CR$^3$R$^4$NR$^5$—

Cyclic beta-keto esters, A2, are either commercially available, or readily prepared by one of the methods outlined in Schemes B1, B2, B3, or B4.

In scheme B1 amine B1.1 is reacted with dialkylacrylate B1.2 to provide the di-addition product, B1.3. Reaction of B1.3 with a base, such as sodium alkoxide, results in a Dieckmann cyclization to produce the cyclic beta keto ester, B1.4.

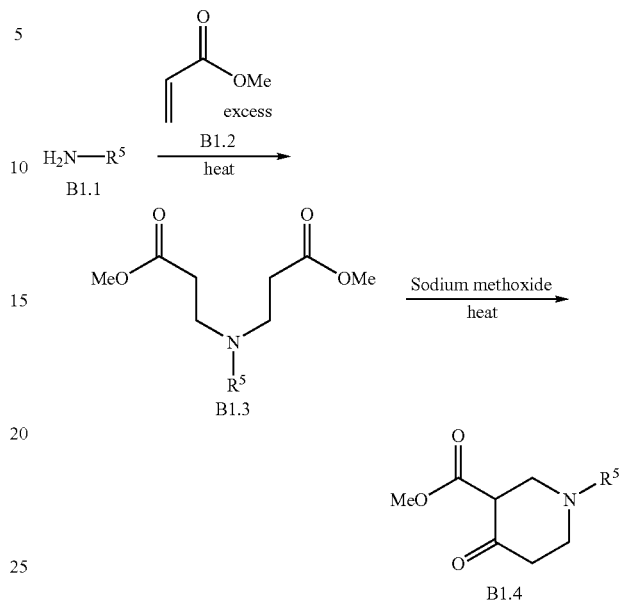

Regioisomeric six-membered cyclic beta-keto esters, B2.7, are either commercially available or prepared by methods reported in the literature which are outlined in Scheme B2. See e.g., Prill, E. et. al., *J. Am. Chem. Soc.*, 55, 1233 (1933). Accordingly, an N-alkylated amino acid, B2.1, is reacted with ethyl bromocrotonate, B2.2, to yield intermediate B2.3 which undergoes double bond reduction to yield B2.4. B2.4 is then subject to standard Dieckmann cyclization conditions to yield intermediate B2.5. If a convenient amine protecting group, such as benzyl group, has been utilized, removal of the protecting group may be accomplished by various means (e.g. hydrogenation or reaction with a chloroformate reagent) to provide the free amine. Regiospecific alkylation of amine B2.6 then provides the desired compound, B2.7. See DaSilva-Goes, A., et. al., *Tetrahedron Lett.*, 1339–40 (1998).

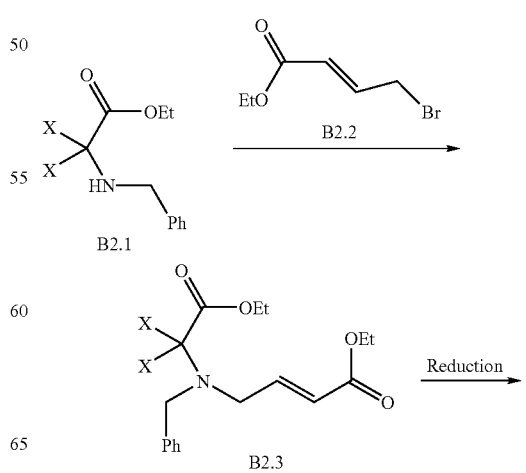

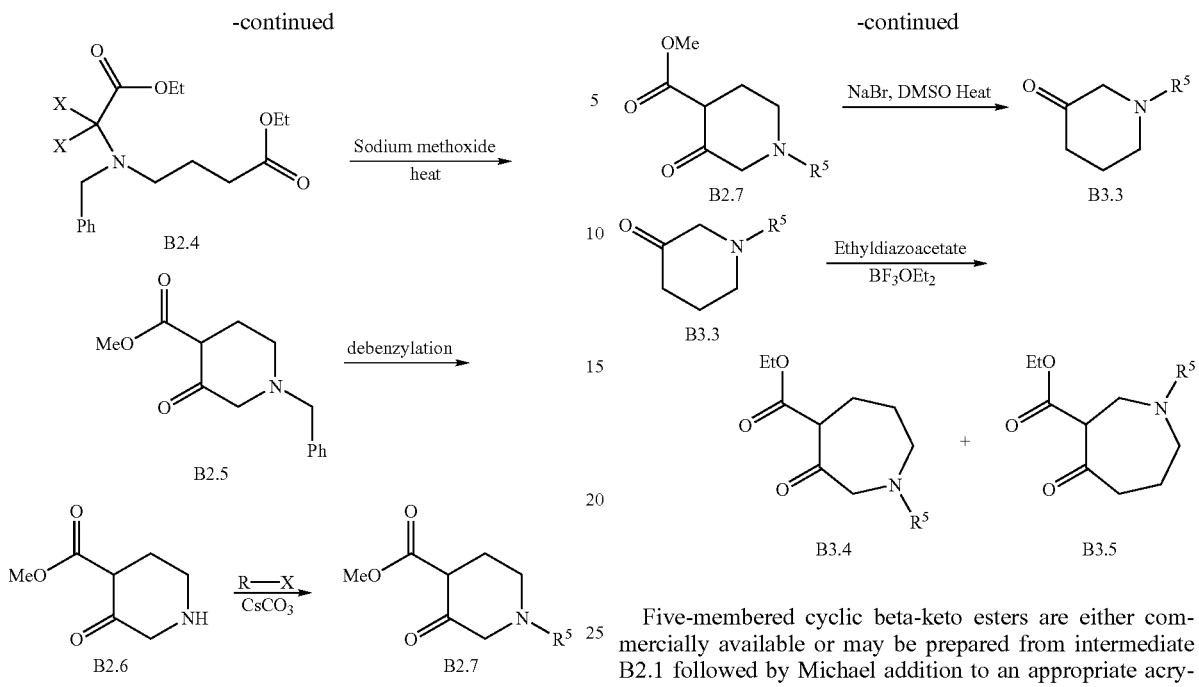

The synthesis of seven-membered cyclic beta-keto esters, B3.2, B3.4 and B3.5, are described in Scheme B3. B3.2 can be prepared from piperidones, B2.1, which are either commercially available or can be prepared by a number of methods including the decarboxylation of B1.4 with reagents such as sodium bromide at elevated temperature. Treatment of piperidone B2.1 with ethyl diazoacetate and boron trifluoride etherate at reduced temperature provides the ring expanded to intermediate, B2.2, useful for the preparation of compounds of Formula IIIa. Non-symmetrical piperidones, B3.3, are either commercially available, have been reported in the literature, or may be prepared by decarboxylation of the intermediate B2.7. See Krosgsgaard-Larsen, P., et al., *Acta Chem. Scand. Ser. B.* 884–88 (1976). B3.3, may then be reacted with ethyl diazoacetate to produce a separable mixture of seven membered ring regioisomers. Selection of the desired regioisomer and reaction as depicted in scheme A is useful for the production of compounds of Formula IIIb or IIIc.

Five-membered cyclic beta-keto esters are either commercially available or may be prepared from intermediate B2.1 followed by Michael addition to an appropriate acrylate, B4.1, to produce the intermediate, B4.2. Internal condensation of B4.2, in the presence of titanium tetrachloride to provide B4.3 has been reported in the literature. Deshmukh, M. N., et. al., *Synth. Comm.*, 26(9), 1657 (1996). Removal of a protecting group, such as a benzyl group, provides a diversity of compounds.

Scheme C outlines the conversion of the ester of Formula I to the amide, of Formula I. Basic hydrolysis of ester C1.1 (e.g. via the use of sodium hydroxide) affords the acid, C2. Alternatively, a protecting group, such as a tert-butyl group (depicted in C1.2), may be readily removed by treatment with trifluoroacetic acid to produce C2. Another alternative is the use of a benzyl protecting group (depicted in C1.3), which may be removed by reaction with hydrogen in the presence of a suitable catalyst, such as palladium on carbon under elevated pressure. Coupling of acid C2 under standard amide bond coupling conditions (EDCI/HOAt) with the appropriate amine, C3, gives the desired amide, C4.

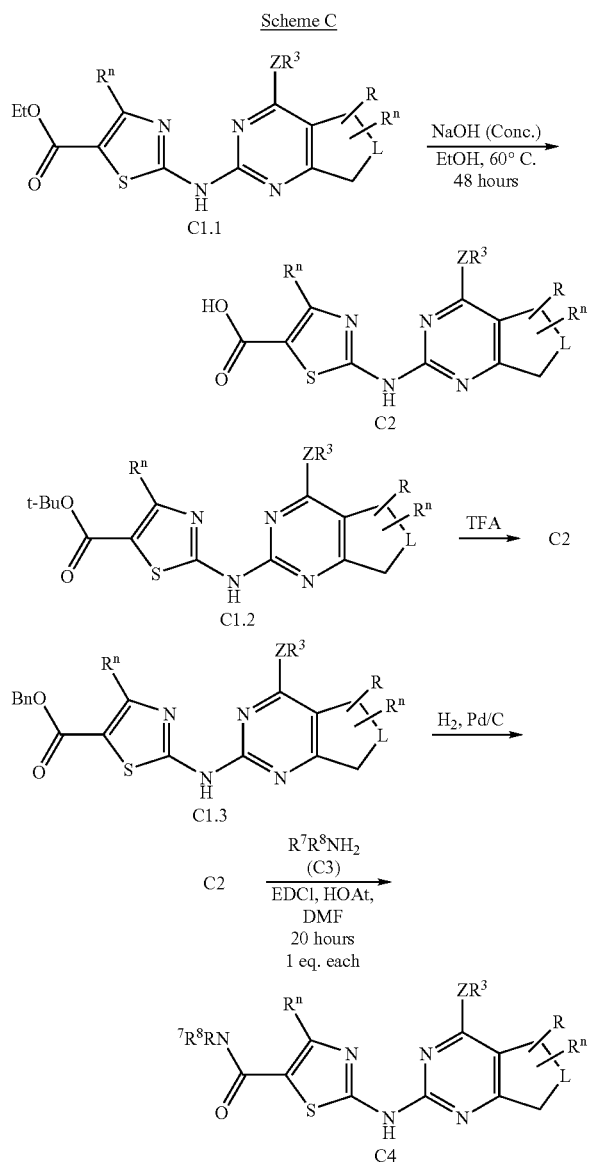

Z = ──NR──, ──O──, ──S──, ──SO$_2$NR──
R, R$^n$ = a substituent
n = an integer
L = ──NR$^5$──, ──NR$^5$CR$^3$R$^4$──, ──CR$^3$R$^4$NR$^5$──,
──CR$^3$R$^4$NR$^5$CR$^3$R$^4$──, ──NR$^5$CR$^3$R$^4$CR$^3$R$^4$──, or
──CR$^3$R$^4$CR$^3$R$^4$NR$^5$──

The substituted guanidines referred to in scheme A, are either commercially available or readily prepared by a number of methods known to one skilled in the art of organic chemistry. As depicted in scheme D1, amine D1.1 may be reacted with a number of reagents such as commercially available 2-3,5-dimethylpyrazole-1-carboxamidine nitrate, D1.2, to provide the desired substituted guanidine, D1.3.

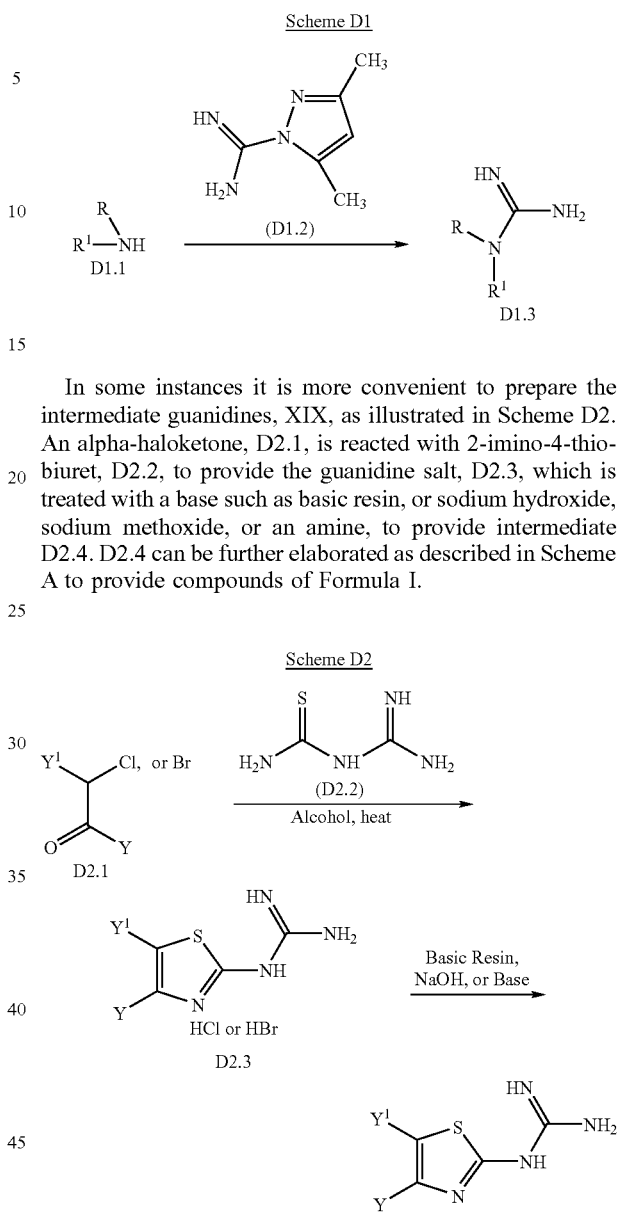

In some instances it is more convenient to prepare the intermediate guanidines, XIX, as illustrated in Scheme D2. An alpha-haloketone, D2.1, is reacted with 2-imino-4-thio-biuret, D2.2, to provide the guanidine salt, D2.3, which is treated with a base such as basic resin, or sodium hydroxide, sodium methoxide, or an amine, to provide intermediate D2.4. D2.4 can be further elaborated as described in Scheme A to provide compounds of Formula I.

The compounds of Formula (I), are useful in the treatment (including prevention, partial alleviation or cure) of leukocyte activation-associated disorders. These disorders include (but are not limited to) transplant rejection (such as organ transplant, acute transplant, xenotransplant or heterograft or homograft such as is employed in burn treatment); protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease;

T-cell-mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (e.g., asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The term "leukocyte activation-associated disorder" or "leukocyte activation-mediated disorder" as used herein includes each of the above referenced diseases or disorders. The compounds of the present invention are useful for treating the aforementioned exemplary disorders irrespective of their etiology.

The present invention thus provides methods for the treatment of leukocyte activation-associated disorders (discussed above) comprising the step of administering to a subject in need thereof of at least one compounds of Formula (I). Other therapeutic agents such as those described below may be employed with the compounds of the present invention. In the methods of the present invention, such other therapeutic agent(s) may be administered prior to, simultaneously with or following the administration of the compound(s) of the present invention.

The methods of treating diseases which would benefit from administering compounds of Formula (I) alone or in combination with each other and/or other suitable therapeutic agents useful in treating such conditions. These agents include, without limitation: immunosuppressants such as cyclosporins (e.g., cyclosporin A), anti-IL-1 agents, such as Anakinra®, the IL-1 receptor antagonist, CTLA4-Ig, antibodies such as anti-ICAM-3, anti-IL-2 receptor (Anti-Tac®), anti-CD45RB, anti-CD2, anti-CD3, anti-CD4, anti-CD80, anti-CD86, monoclonal antibody OKT3, agents blocking the interaction between CD40 and CD154, such as antibodies specific for CD40 and/or CD154 (i.e., CD40L), fusion proteins constructed from CD40 and CD154 (CD40Ig and CD8–CD154), interferon beta, interferon gamma, methotrexate, FK506 (tacrolimus, Prograf®), rapamycin (sirolimus or Rapamune®)mycophenolate mofetil, leflunomide (Arava®), azathioprine and cyclophosphamide, inhibitors, such as nuclear translocation inhibitors, of NF-kappa B function, such as deoxyspergualin (DSG), non-steroidal antiinflammatory drugs (NSAIDs) such as ibuprofen, cyclooxygenase-2 (COX-2) inhibitors such as celecoxib (Celebrex®) and rofecoxib (Vioxx®), or derivatives thereof, steroids such as prednisone or dexamethasone, gold compounds TNF-α inhibitors such as tenidap, anti-TNF antibodies or soluble TNF receptor such as etanercept (Enbrel®), inhibitors of p-38 kinase such as BIRB-796, RO-3201195, VX-850, and VX-750, beta-2 agonists such as albuterol, levalbulterol (Xopenex®), and salmeterol (Serevent®), inhibitors of leukotriene synthesis such as montelukast (Singulair®) and zwaiflukast (Accolate®), and anticholillergic agents such as ipratropium bromide (Atrovent®), PDE4 inhibitors such as Arofyline, Cilomilast, Roflumilast, C-11294A, CDC-801, BAY-19-8004, Cipamfylline, SCH351591, YM-976, PD-189659, Mesiopram, Pumafentrine, CDC-998, IC-485, and KW-4490, and PDE7 inhibitors such as IC242. See Lee, et al., *Cell Signalling*, 14, 277–284, (2002). Other compounds which may be used in combination with compounds of Fomula (I) to treat diseases are disclosed in the following patent documents: WO 0068230, WO 0129049, WO 0132618, WO 0134601, WO 0136425, WO 0174786, WO 0198274, WO 0228847; U.S. Prov. Appl. Ser. Nos. 60/287,964, and 60/355,141; as well as anti-cytokines such as anti-IL-1 mAb or IL-1 receptor agonist; anti-IL-4 or IL-4 receptor fusion proteins; and PTK inhibitors such as those disclosed in U.S. Pat. Nos. 5,990, 109, 6,235,740 and 6,239,133, U.S. Appl. Ser. Nos. 60/065, 042 and. 09/173,413, filed Nov. 10, 1997 and Oct. 15, 1998, respectively. All of the foregoing patents and patent applications are incorporated herein by reference in their entirety.

See also the following documents and references cited therein: Hollenbaugh, D., et al., *J. Immunol. Methods*, 188(1), 1–7 (1995); Hollenbaugh, D., et al., *EMBO J.*, 11(12),4313–4321 (1992); and Moreland, L. W., et al., *New England J. of Medicine*, 337(3), 141–147 (1997).

The above other therapeutic agents, when employed in combination with the compounds of the present invention, may be used, for example, in those amounts indicated in the Physicians' Desk Reference (PDR) or as otherwise determined by one of ordinary skill in the art.

Use of the compounds having Formula (I) of the present invention in treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to asthma, exercise induced asthma, chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis;

serum sickness; uticaria; allergic diseases such as respiratory allergies (asthma, hayfever, allergic rhinitis) or skin allergies; scleracierma; mycosis fungoides; acute inflammatory and respiratory responses (such as acute respiratory distress syndrome and ishchemia/reperfusion injury); dermatomyositis; alopecia areata; chronic actinic dermatitis; eczema; Behcet's disease; Pustulosis palmoplanteris; Pyoderma gangrenum; Sezary's syndrome; atopic dermatitis; systemic schlerosis; and morphea.

The combined activity of the present compounds towards T-cells may be of value in the treatment of any of the aforementioned disorders.

In a particular embodiment, the compounds of the present invention are useful for the treatment of the aforementioned exemplary disorders irrespective of their etiology, for example, in the treatment of transplant rejection, rheumatoid arthritis, multiple sclerosis, chronic obstructive pulmonary disease, inflammatory bowel disease, lupus, graft v. host disease, T-cell mediated hypersensitivity disease, psoriasis, Hashimoto's thyroiditis, Guillain-Barre syndrome, cancer, contact dermatitis, allergic disease such as allergic rhinitis, asthma, ischemic or reperfusion injury, respiratory diseases such as asthma, COPD and bronchitis or atopic dermatitis.

T-Cell Proliferation Assay

Peripheral blood mononuclear cells (PBMC) were isolated from whole blood by density gradient centrifugation over Lymphoprep, 1.077. Cells were plated into 96 well U-bottom plates at $2.5 \times 10_5$ cells/well in 10% FBS RPMI 1640 (Life Technologies/Gibco-BRL) containing 10 ug/ml anti-CD3 (G19-4, Bristol-Myers Squibb P.R.I., Princeton, N.J.) and 1 ug/ml anti-CD28 (9.3, Bristol-Myers Squibb P.R.I.) in the presence and absence of inhibitors. DMSO (used as a solvent for inhibitors) was added to the medium at 0.1% final concentration. The total volume per well was 200 µL. Cells were incubated at 37C. 5% CO2 for 3 days, at which time 0.5 µCi of $^3$H-thymidine was added to each well. Six hours following the addition of $^3$H-thymidine, the plates were harvested onto filter plates, 30 ul EcoLite scintillant (ICN, Costa Mesa, Calif.) was added per well, and plates read on a Top Count-NXT scintillation counter.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells ($2 \times 10^5$/well in U-bottom 96 well plates) were pre-incubated with compounds for 30 min at 37 C prior to addition of lipopolysaccharide (LPS) at a final concentration of 6.25 ng/ml in a total volume of 200 µL. After 4 h at 37° C., 50 µL of supernatant was carefully aspirated for detection of soluble TNFα. Soluble TNFα was detected by ELISA developed by R&D Systems (Minneapolis, Minn.) according to the manufacturer's instructions.

EXAMPLES

The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by example only where the compound is the title compound of the example (for example, "A2" denotes the title compound of Example A2).

| | Abbreviations |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc | tert-butoxycarbonyl |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| M$^+$ | (M + H)$^+$ |
| M$^{+1}$ | (M + H)$^+$ |
| MS | Mass spectrometry |
| n | normal |
| Pd/C | Palladium on carbon |
| Ph | Phenyl |
| Pr | Propyl |
| Ret Time | Retention time |
| rt or RT | Room temperature |
| sat. | Saturated |
| S-Tol-BINAP | (S)-(−)-2,2'-Bis(di-p-tolylphosphino)-1,1'-binapthyl |
| t | tert |
| TFA | Trifluoroacetic acid |
| THF | Tetrahydrofuran |
| YMC | YMC Inc, Wilmington, NC 28403 |

HPLC conditions used to determine retention times; 4 min gradient 0–100% B in A(A; 0.1% TFA in 90/10 water/methanol; B; 0.1% TFA in 10/90 water/methanol) using a YMC turbopack column at with a detection wavelength of 220 nanometeres or 254 nanometers.

Example A1

2-[[4-[[[4-(Methylsulfonyl)phenyl]methyl]amino]-5,6,7,8-tetrahydro-6-methylpyrido[4,3-d]pyrimidin-2-yl]amino]-4-methyl-5-thiazolecarboxylic acid ethyl ester

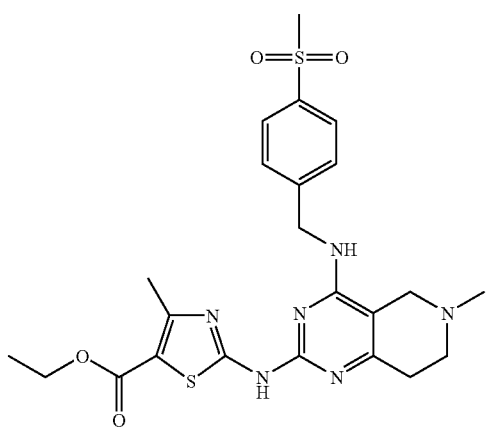

A1.1: N-(3-Methoxy-3-oxopropyl)-N-methyl-β-alanine methyl ester

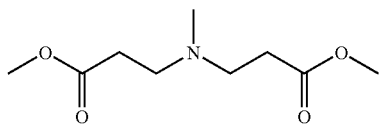

A solution of methyl acrylate (3.79 g, 44 mmol) and methyl amine (2M in methanol, 10 ml, 20 mmol) was heated to 100° C. in a sealed pressure tube for 2 days. The reaction mixture was concentrated to give a crude product which was purified on silica gel column with dichloromethane/methanol (50/1). The fractions which contained the product were concentrated and dried over vacuum pump to yield A1.1 (3.96 g, 86%). $^1$H-NMR (CDCl$_3$) δ: 3.70 (6H, s), 2.74 (4H, t, J=7 Hz), 2.50 (4H, t, J=7 Hz), 2.27 (3H, s).

A1.2: 1-Methyl-4-oxo-3-piperidinecarboxylic acid methyl ester

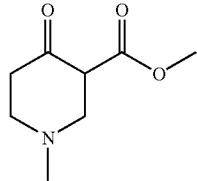

To a solution of sodium methoxide (25% in methanol, 4.74 ml, 20 mmol) in toluene (40 ml) at 110° C. was added A1.1 (2.0 g, 9.84 mmol). The reaction mixture was refluxed for 1 hr and then it was cooled down to room temperature. The reaction mixture was concentrated to give a crude product which was purified on silica gel column with dichloromethane/methanol (20/1). The fractions which contained the product was concentrated and dried over vacuum pump to yield the desired product (1.61 g, 96%). $^1$H-NMR (CD$_3$OD) δ: 3.50 (3H, s), 3.25 (1H, m), 3.09 (1H, m), 2.60–2.70 (1H, m), 2.44–2.51 (1H, m), 2.14–2.34 (5H, m). HPLC: 96%, ret. time=0.18 min., LC/MS (M+H)$^+$=172.

A1.3: 2-[(Aminoiminomethyl)amino]-4-methyl-5-thiazolecarboxylic acid ethyl ester

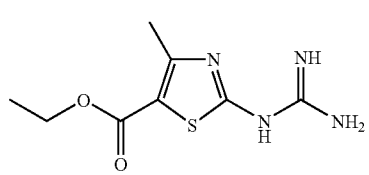

A solution of 2-imino-4-thiobiuret (20.0 g, 0.17 mol), 2-chloroacetoacetate (28 g, 0.17 mol) in ethanol (500 mL) was heated to 100° C. for 4 hours. The reaction mixture was concentrated to half volume and poured into 1 liter of 1N NaOH. The white solid which precipitated out was collected by filtration and dried under vacuum to yield A1.3 (30.5 g, 79%). $^1$H-NMR (DMSO-d$_6$) δ: 4.22 (2H, q, J=7 Hz), 2.50 (3H, merge with DMSO), 1.26 (3H, t, J=7 Hz). HPLC: 97.7%, ret. time=1.619 min., LC/MS (M+H)$^+$=229.

A1.4: 2-(4-Methyl-5-ethoxycarbonylthiazol-2-ylamino)-5,6,7,8-tetrahydro-6-methyl pyrido[4,3-d]pyrimidin-4-ol

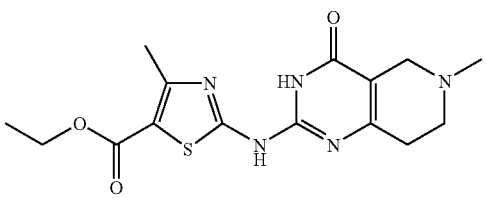

A solution of A1.2 (125 mg, 0.731 mmol), A1.3 (167 mg, 0.731 mmol) and sodium ethoxide(21% in ethanol, 0.989 ml, 2.65 mmol) in DMA was heated to 100° C. for 1 hr and then it was cooled down to RT. The reaction mixture was diluted with 2 mL of water, and neutralized with 1 N HCl. The solid was collected by filtration and dried to yield A1.4 (150 mg, 59%).

A1.5: 2-(4-Methyl-5-ethoxycarbonylthiazol-2-ylamino),4-chloro-5,6,7,8-tetrahydro-6-methyl-pyrido[4,3-d]pyrimidine

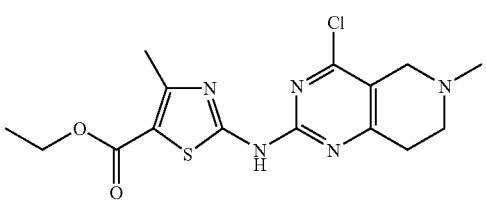

A solution of A1.4 (150 mg, 0.429 mmol) in POCl$_3$ (1 ml) was heated to 100° C. for 2 hours and then it was cooled down to RT which was poured into 10 ml of ice-water. It was neutralized with NaOH to pH about 9. The solid was collected with filtration and then it was added to 10 ml of methanol and stirred about 10 minutes. The solid was filtered off. The mother solution was concentrated to yield the desired product A1.5 (70 mg, 44.3%). LC/MS (M+H)$^+$ =368.

A1.6: 2-[[4-[[[4-(Methylsulfonyl)phenyl]methyl]amino]-5,6,7,8-tetrahydro-6-methylpyrido[4,3-d]pyrimidin-2-yl]amino]-4-methyl-5-thiazolecarboxylic acid ethyl ester A solution of A1.5 (70 mg, 0.19 mmol) and 4-methylsulfonylbenzylamine hydrochloric salt (66 mg, 0.285 mmol), diisopropylethylamine (111 mg, 0.855 mmol) in N-methyl-2-pyrrolidine (2 mL) was heated to 120 to 130° C. for two hours. The reaction mixture was concentrated to yield a crude product which was purified with prep. HPLC (reverse phase) to yield A1(38 mg, 32%). $^1$H-NMR (CD$_3$OD) δ: 7.78 (2H, d, J=8 Hz), 7.52 (2H, d, J=8 Hz), 4.92 (2H, s), 4.17 (2H, q, JJ=7 Hz), 4.03 (2H, m), 3.45 (2H, m), 2.93–2.98 (8H, m), 2.40 (3H, s), 1.18 (3H, t, J=7 Hz). HPLC: 98%, ret. time=1.58 min., LC/MS (M+H)$^+$=517.

Example A2–A23

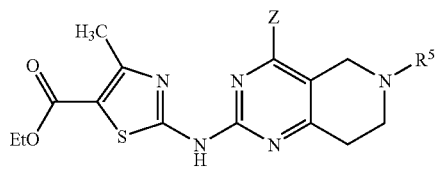

Examples A2 was prepared in a similar manner to that used for Example A1. Example A3 and A4 were prepared in a similar manner to example A1 except intermediate A1.2 was replaced with commercially available methyl 1-benzyl-4-oxo-3-piperdine carboxylate hydrochloride and methyl 4-oxo-3-piperidine carboxylate hydrochloride, and reacted with the appropriate amine corresponding the R$^1$ group. The R2 group was installed after removal of the benzyl group in a manner analogous to that described in the synthesis of example C4, followed by reaction with appropriate reagents.

TABLE A1

| Ex. | Z | R$^5$ | Name | HPLC Retention (min) | MS Reported |
|---|---|---|---|---|---|
| A2 | H$_2$N-S(O)$_2$-C$_6$H$_4$-CH$_2$-NH- | —Me | 2-[[4-[[[4-(Aminosulfonyl)phenyl]methyl]-amino]-5,6,7,8-tetrahydro-6-methylpyrido[4,3-d]pyrimidin-2-yl]amino]-4-methyl-5-thiazolecarboxylic acid ethyl ester | 1.467 | 518.12 |
| A3 | H$_2$N-S(O)$_2$-C$_6$H$_4$-CH$_2$-NH- | —Bn | 2-[[4-[[[4-(Aminosulfonyl)phenyl]methyl]-amino]-5,6,7,8-tetrahydro-6-(phenylmethyl)pyrido[4,3-d]pyrimidin-2-yl]amino]-4-methyl-5-thiazolecarboxylic acid ethyl ester | 1.94 | 594.39 |
| A4 | H$_2$N-S(O)$_2$-C$_6$H$_4$-CH$_2$-NH- | —H | 2-[[4-[[[4-(Aminosulfonyl)phenyl]methyl]-amino]-5,6,7,8-tetrahydropyrido[4,3-d]pyrimidin-2-yl]amino]-4-methyl-5-thiazolecarboxylic acid ethyl ester | 1.46 | 503.59 |
| A5 | H$_2$N-S(O)$_2$-C$_6$H$_4$-CH$_2$-NH- | —C(O)CH$_2$OC(O)CH$_3$ | 2-[[6-[(Acetyloxy)acetyl]-4-[[[4-(aminosulfonyl)phenyl]methyl]amino]-5,6,7,8-tetrahydropyrido[4,3-d]pyrimidin-2-yl]amino]-4-methyl-5-thiazolecarboxylic acid ethyl ester | 2.26 | 604.15 |
| A6 | H$_2$N-S(O)$_2$-C$_6$H$_4$-CH$_2$-NH- | —C(O)CH$_2$OH | 2-[[4-[[[4-(Aminosulfonyl)phenyl]-methyl]amino]-5,6,7,8-tetrahydro-6-(hydroxyacetyl)pyrido[4,3-d]pyrimidin-2-yl]amino]-4-methyl-5-thiazolecarboxylic acid ethyl ester | 2.09 | 562.37 |
| A7 | H$_2$N-S(O)$_2$-C$_6$H$_4$-CH$_2$-NH- | —C(O)OEt | 2-[[4-[[[4-(Aminosulfonyl)phenyl]-methyl]amino]-5,6,7,8-tetrahydro-6-(ethoxycarbonyl)pyrido[4,3-d]pyrimidin-2-yl]amino]-4-methyl-5-thiazolecarboxylic acid ethyl ester | 1.45 | 576.48 |

TABLE A1-continued

| Ex. | Z | R⁵ | Name | HPLC Retention (min) | MS Reported |
|---|---|---|---|---|---|
| A8 | 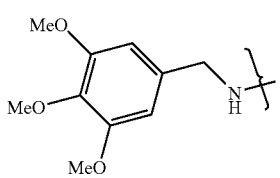 |  | 2-[[4-[[[3,4,5-Trimethoxyphenyl]-methyl]amino]-5,6,7,8-tetrahydro-6-(formyl)pyrido[4,3-d]pyrimidin-2-yl]amino]-4-methyl-5-thiazolecarboxylic acid ethyl ester | 1.48 | 543.47 |
| A9 | 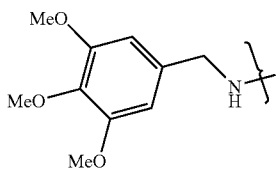 | 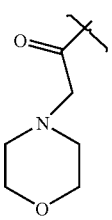 | 2-[[4-[[[3,4,5-Trimethoxyphenyl]-methyl]amino]-5,6,7,8-tetrahydro-6-(morpholin-4-ylmethylcarbonyl)pyrido[4,3-d]pyrimidin-2-yl]amino]-4-methyl-5-thiazolecarboxylic acid ethyl ester | 1.36 | 642.48 |
| A10 | 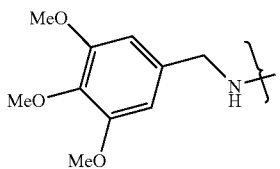 | 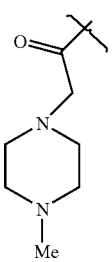 | 2-[[4-[[[3,4,5-Trimethoxyphenyl]-methyl]amino]-5,6,7,8-tetrahydro-6-(4-methylpiperazin-1-ylmethylcarbonyl)-pyrido[4,3-d]pyrimidin-2-yl]amino]-4-methyl-5-thiazolecarboxylic acid ethyl ester | 1.38 | 655.48 |
| A11 | 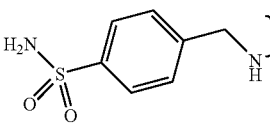 | 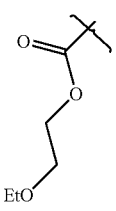 | 2-[[4-[[[4-(Aminosulfonyl)phenyl]-methyl]amino]-5,6,7,8-tetrahydro-6-((2-ethoxy)ethoxycarbonyl)pyrido[4,3-d]pyrimidin-2-yl]amino]-4-methyl-5-thiazolecarboxylic acid ethyl ester | 1.47 | 620.41 |
| A12 | 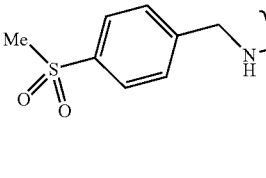 | 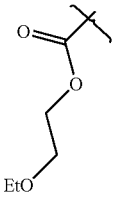 | 2-[[4-[[[4-(Methylsulfonyl)phenyl]-methyl]amino]-5,6,7,8-tetrahydro-6-((2-ethoxy)ethoxycarbonyl)pyrido[4,3-d]pyrimidin-2-yl]amino]-4-methyl-5-thiazolecarboxylic acid ethyl ester | 1.49 | 619.42 |
| A13 | 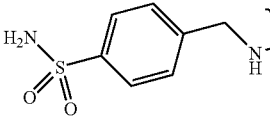 | —CN | 2-[[4-[[[4-(Aminosulfonyl)phenyl]-methyl]amino]-5,6,7,8-tetrahydro-6-(cyano)pyrido[4,3-d]pyrimidin-2-yl]amino]-4-methyl-5-thiazolecarboxylic acid ethyl ester | 1.27 | 529.44 |
| A14 |  | 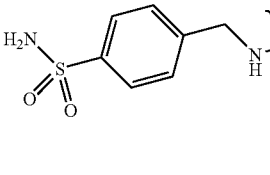 | 2-[[4-[[[4-(Aminosulfonyl)phenyl]-methyl]amino]-5,6,7,8-tetrahydro-6-(allyloxycarbonyl)pyrido[4,3-d]pyrimidin-2-yl]amino]-4-methyl-5-thiazolecarboxylic acid ethyl ester | 1.50 | 588.43 |

TABLE A1-continued

| Ex. | Z | R⁵ | Name | HPLC Retention (min) | MS Reported |
|---|---|---|---|---|---|
| A15 | 4-(aminosulfonyl)benzyl-NH- | -C(=O)H | 2-[[4-[[[4-(Aminosulfonyl)phenyl]-methyl]amino]-5,6,7,8-tetrahydro-6-(allyloxycarbonyl)pyrido[4,3-d]pyrimidin-2-yl]amino]-4-methyl-5-thiazolecarboxylic acid ethyl ester | 1.23 | 532.42 |
| A16 | 4-(aminosulfonyl)benzyl-NH- | -C(=O)OPh | 2-[[4-[[[4-(Aminosulfonyl)phenyl]-methyl]amino]-5,6,7,8-tetrahydro-6-(phenyloxycarbonyl)pyrido[4,3-d]pyrimidin-2-yl]amino]-4-methyl-5-thiazolecarboxylic acid ethyl ester | 1.56 | 624.42 |
| A17 | 4-(aminosulfonyl)benzyl-NH- | -C(=O)C(=O)OMe | 2-[[4-[[[4-(Aminosulfonyl)phenyl]-methyl]amino]-5,6,7,8-tetrahydro-6-(methoxycarbonylcarbonyl)pyrido[4,3-d]pyrimidin-2-yl]amino]-4-methyl-5-thiazolecarboxylic acid ethyl ester | 1.34 | 590.44 |
| A18 | 4-(aminosulfonyl)benzyl-NH- | -C(=O)CH₂NMe₂ | 2-[[4-[[[4-(Aminosulfonyl)phenyl]-methyl]amino]-5,6,7,8-tetrahydro-6-(dimethylaminomethylcarbonyl)pyrido[4,3-d]pyrimidin-2-yl]amino]-4-methyl-5-thiazolecarboxylic acid ethyl ester | 1.12 | 589.48 |
| A19 | 4-(aminosulfonyl)benzyl-NH- | -C(=O)CH₂CH₂COOH | 2-[[4-[[[4-(Aminosulfonyl)phenyl]-methyl]amino]-5,6,7,8-tetrahydro-6-(carboxyethylcarbonyl)pyrido[4,3-d]pyrimidin-2-yl]amino]-4-methyl-5-thiazolecarboxylic acid ethyl ester | 1.27 | 604.43 |
| A20 | 3,4,5-trimethoxybenzyl-NH- | -CH₂-cyclopropyl | 2-[[4-[[[3,4,5-Trimethoxyphenyl]-methyl]amino]-5,6,7,8-tetrahydro-6-(cyclopropylmethyl)pyrido[4,3-d]pyrimidin-2-yl]amino]-4-methyl-5-thiazolecarboxylic acid ethyl ester | 1.63 | 569.57 |
| A21 | 4-(aminosulfonyl)benzyl-NH- | -C(=O)O-(3-tetrahydrofuranyl) | 2-[[4-[[[4-(Aminosulfonyl)phenyl]-methyl]amino]-5,6,7,8-tetrahydro-6((3-tetrahydrofuranyl)oxocarbonyl)pyrido[4,3-d]pyrimidin-2-yl]amino]-4-methyl-5-thiazolecarboxylic acid ethyl ester | 1.38 | 618.46 |
| A22 | 4-(aminosulfonyl)benzyl-NH- | -CH₂-cyclopropyl | 2-[[4-[[[4-(Aminosulfonyl)phenyl]-methyl]amino]-5,6,7,8-tetrahydro-6-(cyclopropylmethyl)pyrido[4,3-d]pyrimidin-2-yl]amino]-4-methyl-5-thiazolecarboxylic acid ethyl ester | 1.10 | 558.49 |
| A23 | 3,4,5-trimethoxybenzyl-NH- | -C(=O)CH₂OH | 2-[[4-[[[3,4,5-Trimethoxyphenyl]-methyl]amino]-5,6,7,8-tetrahydro-6-(hydroxyacetyl)pyrido[4,3-d]pyrimidin-2-yl]amino]-4-methyl-5-thiazolecarboxylic acid ethyl ester | 1.44 | 573.51 |

TABLE A1-continued

| Ex. | Z | R⁵ | Name | HPLC Retention (min) | MS Reported |
|---|---|---|---|---|---|
| A24 | 3,4-dimethoxybenzyl-NH- | 2-propenyl | 2-[[4-[[[3,4,-Dimethoxyphenyl]-methyl]amino]-5,6,7,8-tetrahydro-6-(2-propenyl)pyrido[4,3-d]pyrimidin-2-yl]amino]-4-methyl-5-thiazolecarboxylic acid ethyl ester | 1.16[a] | 525.31 |
| A25 | 4-(aminosulfonyl)benzyl-NH- | methylsulfonyl | 2-[[4-[[[3,4,5-Trimethoxyphenyl]-methyl]amino]-5,6,7,8-tetrahydro-6-(methylsulfonyl)pyrido[4,3-d]pyrimidin-2-yl]amino]-4-methyl-5-thiazolecarboxylic acid ethyl ester | 1.26[a] | 593.21 |

[a]HPLC conditions used to determine retention times; 2 min gradient 0–100% B in A(A; 0.1% TFA in 90/10 water/methanol; B; 0.1% TFA in 10/90 water/methanol) using a Phenomenex S5 ® column at 254 nm.

Example A26–A28

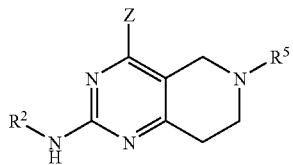

The compounds in Table A2 were prepared using the appropriate guanidine corresponding to A1.3. A26 and A27 were elaborated as described for A3. A28 was elaborated as described for the synthesis of example C4.1 with the exception that benzylchloroformate was replaced with ethylchoroformate.

TABLE A2

| Ex. | Z | R⁵ | R² | Name | HPLC Retention (min) | MS Reported |
|---|---|---|---|---|---|---|
| A26 | morpholinyl | —Bn | quinolinyl | 6-[[4-morpholinyl-5,6,7,8-tetrahydro-6-(phenylmethyl)pyrido[4,3-d]pyrimidin-2-yl]amino]-quinoline | 0.77 | 454.35 |
| A27 | 4-(methylsulfonyl)benzyl-NH- | —Bn | 4-(1-methylimidazol-5-yl)phenyl | 1-[[4-[[[4-(Aminosulfonyl)phenyl]-methyl]amino]-5,6,7,8-tetrahydro-6-(phenylmethyl)pyrido[4,3-d]pyrimidin-2-yl]amino]-4-[(1-methyl)imidazol-5yl]benzene | 0.82 | 581.52 |

TABLE A2-continued

| Ex. | Z | R⁵ | R² | Name | HPLC Retention (min) | MS Reported |
|---|---|---|---|---|---|---|
| A26 | 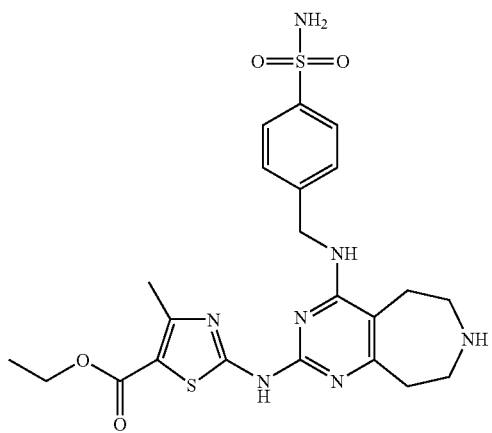 | | | 2-[[4-[[[4-(Methylsulfonyl)phenyl]-methyl]amino]-5,6,7,8-tetrahydro-6-(ethoxycarbonyl)pyrido[4,3-d]pyrimidin-2-yl]amino]-4-methyl-5-thiazolecarboxylic acid methyl amide | 1.17 | 560.46 |

HPLC conditions used to determine retention times; 2 min gradient 0–100% B in A(A; 0.1% TFA in 90/10 water/methanol; B; 0.1% TFA in 10/90 water/methanol) using a Phenomenex S5 ® column at 254 nm.

Example B1

2-[[4-[[[4-(Aminosulfonyl)phenyl]methyl]amino]-6,7,8,9-tetrahydro-5H-pyrimido[4,5-d]azepin-2-yl]amino]-4-methyl-5-thiazolecarboxylic acid ethyl ester

B1

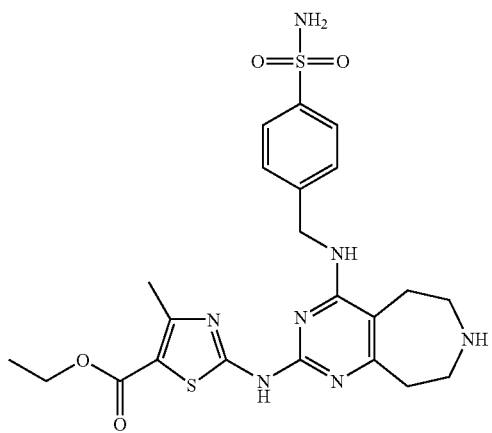

B1.1: Hexahydro-5-oxo-1H-Azepine-1,4-dicarboxylic Acid 4-tertbutyl 1-methyl ester

B1.1

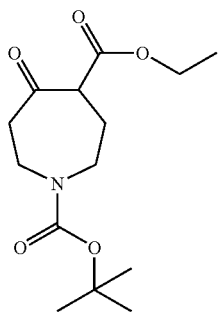

A solution of commercially available N-tertbutoxycarbonyl-4-piperidone (500 mg, 2.46 mmol) in 2 mL of ethyl ether (2 mL) was simultaneously added boron trifluoride etherate (349 mg, 2.46 mmol) and ethyl diazoacetate dropwise (371 mg, 3.25 mmol) at −25° C. to −30° C. The reaction mixture was maintained at −25° C. to −30° C. for one hour and then it was warmed to RT. The reaction mixture was diluted with ethyl ether (30 ml) and was washed with saturated Na₂CO₃ solution (20 mL) and the organic layer dried over sodium sulfate. Filtration and concentration to yield a crude product which was purified on silica gel column with dichloromethane/methanol (50/1 to 20/1) to yield B1.1 (662 mg, 94.4%). HPLC: 91%.

B1.2: 2-(4-Methyl-5-ethoxycarbonylthiazol-2-ylamino)-5,6,8,9-tetrahydro-7-tertbutyloxycarbonylpyrido[4,5-d]azepin-4-ol

B1.2

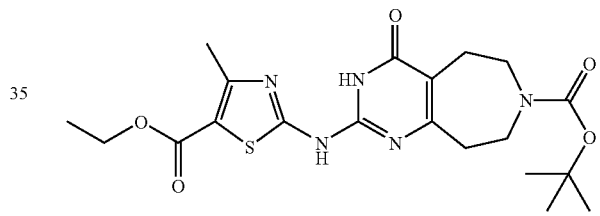

A solution of A1.3 (110 mg, 0.485 mmol) and sodium ethoxide (21% in ethanol, 0.656 ml, 1.76 mmol) in ethanol (2 ml) was heated to 100° C. for half an hour and then it was cooled down to RT which was added B1.1 (138 mg, 0.485 mmol). The reaction mixture was heated to 100° C. for 2 days. It was concentrated to yield a crude product which was diluted with 2 mL of water and neutralized with 1 N HCl. The solid was collected by filtration and stirred with anhydrous methanol for 10 minutes. The resulting solid was collected by filtration to yield B1.2 (77 mg, 35%). LC/MS (M+H)⁺=450.

B1.3: 4-Chloro-2-(4-methyl-5-ethoxycarbonylthiazol-2-ylamino)-5,6,8,9-tetrahydro-7H-pyrido[4,5-d]azepine

B1.3

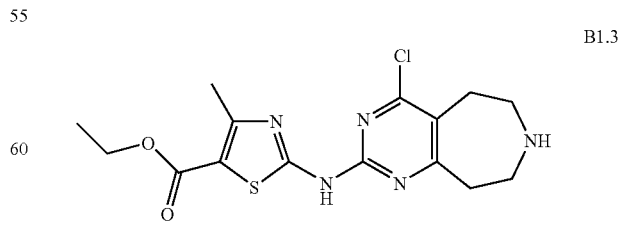

A solution of B1.2 (77 mg, 0.172 mmol) in POCl₃ (0.5 ml) was heated to 100° C. for 16 hours and then it was cooled down to RT which was poured into 5 ml of ice-water. It was neutralized with NaOH to pH about 9. The solid was collected by filtration and then it was added to 3 mL of methanol and stirred about 20 minutes. The solid was collected to yield B1.3 (67 mg). LC/MS (M+H)$^+$=368.

B1.4: 2-[[4-[[[4-(Aminosulfonyl)phenyl]methyl]amino]-6,7,8,9-tetrahydro-5H-pyrimido[4,5-d]azepin-2-yl]amino]-4-methyl-5-thiazolecarboxylic acid ethyl ester A solution of B1.3 (20 mg, 0.0544 mmol) and p-aminomethylbenzenesulfonamide hydrochloric salt (24 mg, 0.109 mmol), diisopropylethylamine (57 uL, 0.326 mmol) in N-methyl-2-pyrrolidine (0.5 ml) was heated to 120 to 130° C. for an hour. The reaction mixture was concentrated to yield a crude product which was purified with prep. HPLC (reverse phase) to yield B1 (2.5 mg, 9%). $^1$H-NMR (CD$_3$OD) δ: 7.86 (2H, d, J=8 Hz), 7.56 (2H, d, J=8 Hz), 5.09 (2H, s), 4.31 (2H, q, JJ=7 Hz), 3.44–3.45 (4H, m), 3.20–3.26 (4H, m), 3.08–3.14 (4H, m), 2.54 (3H, s), 1.32 (3H, t, J=7 Hz). HPLC: 98%, ret. time=1.593 min., LC/MS (M+H)$^+$=518.

Example B2–B4

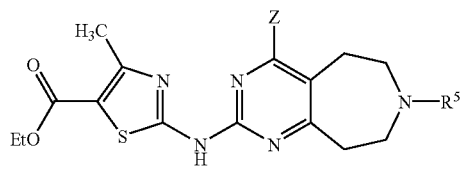

Examples B2 to B4 were prepared in a similar manner to that used for Example B1, with the exception that the 7-amine position was reacted with an appropriate acid chloride.

Example C1

4-Methyl-2-[[5,6,7,8-tetrahydro-7-(phenylmethyl)-4-(1-piperazinyl)pyrido[3,4-d]pyrimidin-2-yl]amino]-5-thiazolecarboxylic acid ethyl ester

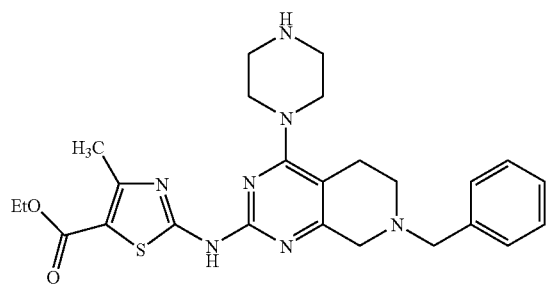

C1.1: 2-(4-Methyl-5-ethoxycarbonylthiazol-2-ylamino)-5,6,7,8-tetrahydro-7-(phenylmethyl)pyrido[3,4-d]pyrimidin-4-ol

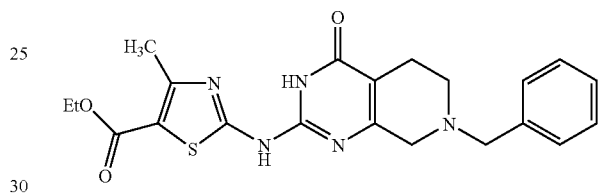

A solution of ethyl 1-benzyl-3-oxo-piperidinecarboxylate.HCl (2.90 g, 9.74 mmol), A1.3 (2.0 g, 8.8 mmol) and sodium ethoxide (21% in ethanol, 13.1 ml, 35.2 mmol) in ethanol (40 ml) was heated to 100° C. for 2 hrs and then it was cooled down to RT which was concentrated to yield a crude product. It was added 100 ml of water which was

TABLE B

| Ex. | Z | R$^5$ | Name | HPLC Retention (min) | MS Reported |
|---|---|---|---|---|---|
| B2 | H$_2$N-S(O)$_2$-C$_6$H$_4$-CH$_2$-NH- | -C(O)-CH$_2$-OH | 4-Methyl-2-[[6,7,8,9-tetrahydro-7-(hydroxyacetyl)-4-[[[4-(methylsulfonyl)phenylmethyl]-amino]-5H-pyrimido[4,5-d]azepin-2-yl]amino]-5-thiazolecarboxylic acid ethyl ester | 2.19 | 575.13 |
| B3 | H$_2$N-S(O)$_2$-C$_6$H$_4$-CH$_2$-NH- | -C(O)-CH$_2$-morpholinyl | 4-Methyl-2-[[6,7,8,9-tetrahydro-4-[[[4-(methylsulfonyl)phenyl]-methyl]amino]-7-(4-morpholinylacetyl)-5H-pyrimido[4,5-d]azepin-2-yl]amino]-5-thiazolecarboxylic acid ethyl ester | 1.77 | 644.16 |
| B4 | H$_2$N-S(O)$_2$-C$_6$H$_4$-CH$_2$-NH- | -C(O)-CH$_2$-O-C(O)-CH$_3$ | 2-[[7-[(Acetyloxy)acetyl]-6,7,8,9-tetrahydro-4-[[[4-(methylsulfonyl)phenyl]methyl]-amino]-5H-pyrimido[4,5-d]azepin-2-yl]amino]-4-methyl-5-thiazolecarboxylic acid ethyl ester | 2.30 | 617.15 | neutralized with 1 N HCl until PH about 7. The solid was collected by filtration and dried under vacuum to yield C1.1 (3.14 g, 84%). LC/MS (M+H)+=426.48.

C1.2: 2-(4-Methyl-5-ethoxycarbonylthiazol-2-ylamino), 4-chloro-5,6,7,8-tetrahydro-7-(phenylmethyl)pyrido[3,4-d] pyrimidine

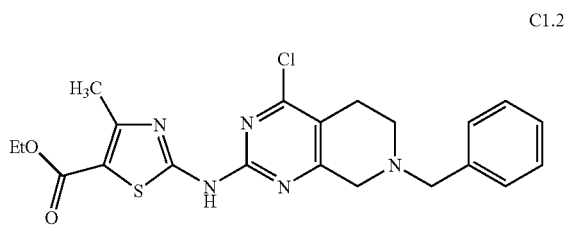

C1.2

A solution of C1.1 (3.14 g, 7.38 mmol) in POCl₃ (25 ml) was heated to 100° C. for 1 hour and then it was cooled down to RT which was poured into 100 ml of ice-water. The reaction mixture was neutralized with 1 N sodium hydroxide to about pH 9. The solid was filtered and dried under vacuum to yield C1.2 (2.80 g, 86%). to LC/MS (M+H)+=444.08.

C1.3: 4-Methyl-2-[[5,6,7,8-tetrahydro-7-(phenylmethyl)-4-(4-tertbutyloxycarbonyl-1-piperazinyl)pyrido[3,4-d]pyrimidin-2-yl]amino]-5-thiazolecarboxylic acid ethyl ester

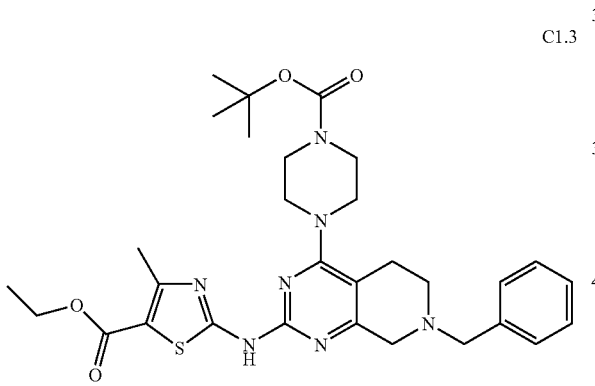

C1.3

A solution of C1.2 (100 mg, 0.225 mmol) and 1-tertbutyloxycarbonylpiperazine (45 mg, 0.236 mmol), diisopropylethylamine (0.137 ml, 0.785 mmol) in N-methyl-2-pyrrolidine (1 mL) was heated to 120 to 130° C. for one hour. The reaction mixture was concentrated under reduced pressure to yield a crude product which was added 2 mL of methanol and stirred for 10 minutes during which time a solid precipitated. The solid was collected by filtration and dried under vacuum to yield C1.3 (66 mg, 49%). ¹H-NMR (DMSO) δ: 7.26–7.39 (5H, m), 4.21 (2H, q, J=7 Hz), 3.67 (2H, s), 2.57–3.60 (14H, m), 2.50 (3H, merge with DMSO), 1.42 (9H, s), 1.29 (3H, t, J=7 Hz). HPLC: 90%, ret. time=3.24 min., LC/MS (M+H)+=594.20.

C1.4: 4-Methyl-2-[[5,6,7,8-tetrahydro-7-(phenylmethyl)-4-(1-piperazinyl)pyrido [3,4-d]pyrimidin-2-yl]amino]-5-thiazolecarboxylic acid ethyl ester To a solution of C1.3 (40 mg, 0.0674 mmol) in dichloromethane (0.5 mL) was added trifluoroacetic acid (0.5 mL) which was stirred at RT for half an hour. The reaction mixture was concentrated to yield a crude product which was added 5 mL of ethyl ether. The solid was collected and dried under vacuum to yield C1 (46.6 mg, 99%). ¹H-NMR (CD₃OD) δ: 7.26–7.44 (5H, m), 4.16–4.28 (4H, m), 3.67 (2H, s), 2.00–4.00 (17H, m), 1.24 (3H, t, J=7 Hz). HPLC: 96%, ret. time=1.92 min., LC/MS (M+H)+=494.15.

Example C2–C3

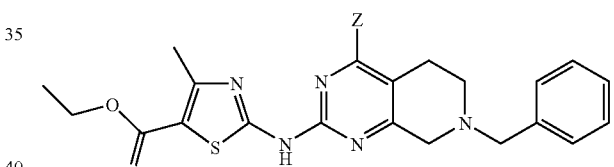

Examples C2 to C3 were prepared in a similar manner to that used for Example C1 using appropriate reagents.

TABLE C1

| Ex. | Z | Name | HPLC Retention[a] (min) | MS Reported |
|---|---|---|---|---|
| C2 | 4-methylsulfonylphenyl-CH₂-NH- | 4-Methyl-2-[[5,6,7,8-tetrahydro-7-(phenylmethyl)-4-[4-(methylsulfonyl)phenyl]methyl]amino]-pyrido[3,4-d]pyrimidin-2-yl]amino]-5-thiazolecarboxylic acid ethyl ester | 2.32 | 593.10 |
| C3 | 4-aminosulfonylphenyl-CH₂-NH- | 4-Methyl-2-[[5,6,7,8-tetrahydro-7-(phenylmethyl)-4-[4-(aminosulfonyl)phenyl]methyl]amino]pyrido[3,4-d]pyrimidin-2-yl]amino]-5-thiazolecarboxylic acid ethyl ester | 2.24 | 594.30 |

[a]HPLC conditions used to determine retention times; 4 min gradient 0–100% B in A(A; 0.1% TFA in 90/10 water/methanol; B; 0.1% TFA in 10/90 water/methanol) using a YMC turbopack column at 254 nm.

Example C4

4-Methyl-2-[[5,6,7,8-tetrahydro-7-((3,4-(dimethoxy)phenyl)methyl)-4-(1-piperazinyl)pyrido[3,4-d]pyrimidin-2-yl]amino]-5-thiazolecarboxylic acid ethyl ester

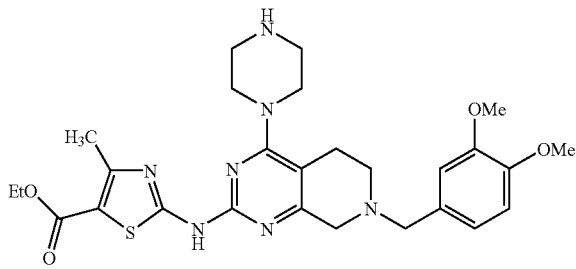

C4.1: 4-Methyl-2-[[5,6,7,8-tetrahydro-7-benzyloxycarbonyl-4-(4-tertbutyloxycarbonyl-1-piperazinyl)pyrido[3,4-d]pyrimidin-2-yl]amino]-5-thiazolecarboxylic acid ethyl ester

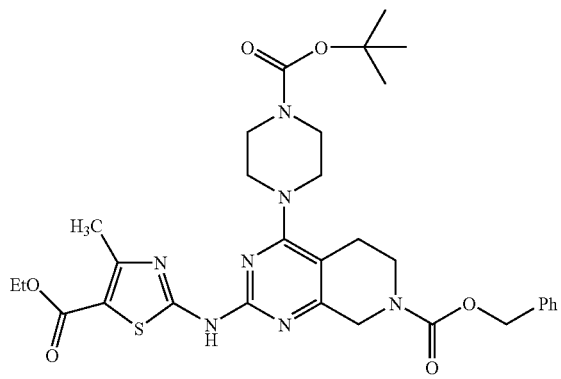

C1.3 (250 mg, 0.42 mmol) was dissolved in dichloroethane, and benzyl chloroformate (200 mg, 1.1 mmol) was added and the reaction mixture refluxed overnight. The reaction mixture was concentrated and purified by silica gel column chromatography to yield C4.1 (220 mg, 82%). (M+H)$^+$=638.51.

C4.2: 4-Methyl-2-[[5,6,7,8-tetrahydro-4-(4-tertbutyloxycarbonyl -1-piperazinyl)pyrido[3,4-d]pyrimidin-2-yl]amino]-5-thiazolecarboxylic acid ethyl ester

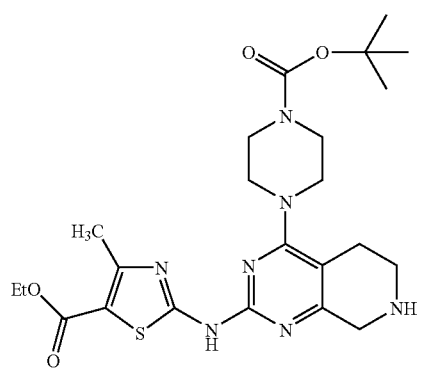

C4.1 (210 mg, 0.33 mmol) was dissolved in 10 mL of acetic acid and 220 mg of 10% palladium on carbon was cautiously added under an inert atmosphere. The reaction mixture was hydrogenated overnight (18 h) at 50 psi using a Parr apparatus. The reaction mixture was filtered, concentrated and purified by prep HPCL to yield C4.2 (114 mg, 70%) as an oil. $^1$H-NMR (CD$_3$OD) δ: 4.15–4.25 (4H, m), 3.50–3.65 (8H, m), 3.50 (2H, m), 2.92 (2H, m), 2.48 (3H, s), 1.40 (9H, s), 1.27 (3H, t, J=7 Hz). (M+H)$^+$=504.18.

C4.3: 4-Methyl-2-[[5,6,7,8-tetrahydro-7-((3,4-(dimethoxy)phenyl)methyl)-4-(4-tertbutyloxycarbonyl-1-piperazinyl)pyrido[3,4-d]pyrimidin-2-yl]amino]-5-thiazolecarboxylic acid ethyl ester

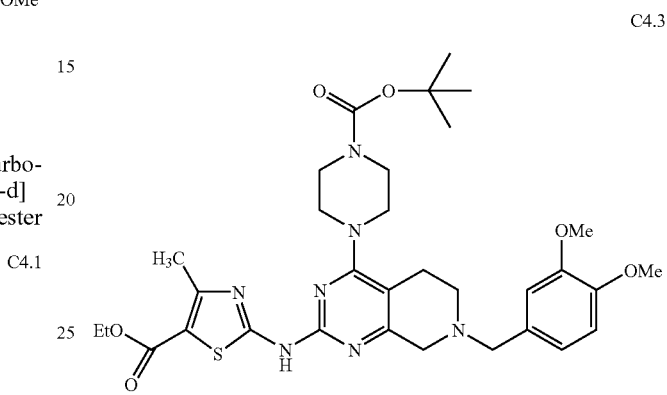

3,4-Dimethoxybenzaldehyde (7 mg, 0.040 mmol), C4.2 (20 mg, 0.040 mmol), and triacetoxyborohydride (17 mg, 0.077 mmol) were suspended in dichloroethane, and stirred at room temperature overnight. The reaction mixture was concentrated, and purified by preparatory HPLC to yield C4.3 (22 mg, 85%). $^1$H-NMR (CDCl$_3$) δ: 6.60–6.80 (3H, m), 4.05–4.25 (6H, m), 3.71 (3H, s), 3.72 (3H, s) 3.50–3.65 (8H, m), 2.55–3.45 (4H, m), 2.50 (3H, s), 1.30 (9H, s), 1.22 (3H, t, J=7 Hz). (M+H)$^+$=654.25.

C4.4: 4-Methyl-2-[[5,6,7,8-tetrahydro-7-((3,4-(dimethoxy)phenyl)methyl)-4-(1-piperazinyl)pyrido[3,4-d]pyrimidin-2-yl]amino]-5-thiazolecarboxylic acid ethyl ester C4.3 (14 mg, 0.021 mmol) was dissolved in 0.5 mL of trifluoroacetic acid and stirred at room temperature for 0.5 h. The solvent was evaporated to provided C4.4 (12 mg, 100%).

$^1$H-NMR (CD$_3$OD) δ: 6.85–7.05 (3H, m), 4.33 (2H, s), 4.05–4.20 (4H, m), 3.75 (3H, s), 3.73 (3H, s) 3.65 (4H, m), 3.16 (2H, merge with CD$_3$OD)), 2.85 (2H, m), 2.42 (3H, s), 1.22 (3H, t, J=7 Hz). (M+H)$^+$=554.49.

Example C5–C24

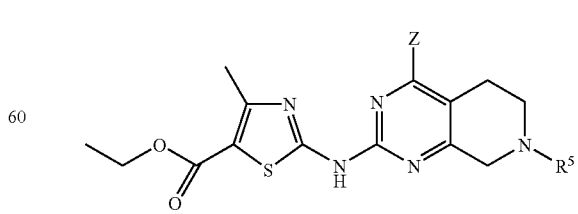

Examples C5 to C24 were prepared in a similar manner to that used for Example C4 using appropriate reagents.

TABLE C2

| Ex. | R⁵ | Z | Name | HPLC Retention (min) | MS Reported |
|---|---|---|---|---|---|
| C5 | 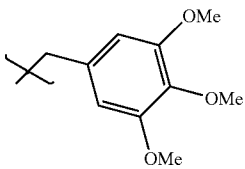 | 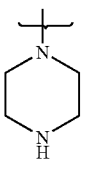 | 4-Methyl-2-[[5,6,7,8-tetrahydro-7-((3,4,5-(trimethoxy)phenyl)methyl)-4-(1-piperazinyl)pyrido[3,4-d]pyrimidin-2-yl]amino]-5-thiazolecarboxylic acid ethyl ester | 1.94 | 584.18 |
| C6 | 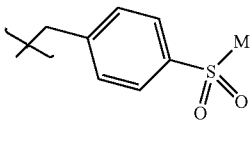 | 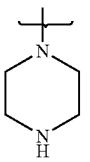 | 4-Methyl-2-[[5,6,7,8-tetrahydro-7-((4-(methyl-sulfonyl)phenyl)methyl)-4-(1-piperazinyl)pyrido[3,4-d]pyrimidin-2-yl]amino]-5-thiazolecarboxylic acid ethyl ester | 1.69 | 572.16 |
| C7 | 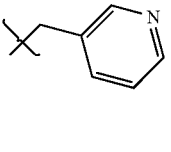 | 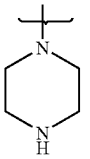 | 4-Methyl-2-[[5,6,7,8-tetrahydro-7-((3-pyridyl)methyl)-4-(1-piperazinyl)pyrido[3,4-d]pyrimidin-2-yl]amino]-5-thiazolecarboxylic acid ethyl ester | 1.31 | 495.13 |
| C8 | 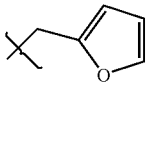 | 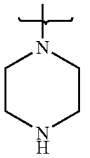 | 4-Methyl-2-[[5,6,7,8-tetrahydro-7-((2-furanyl)methyl)-4-(1-piperazinyl)pyrido[3,4-d]pyrimidin-2-yl]amino]-5-thiazolecarboxylic acid ethyl ester | 1.75 | 484.14 |
| C9 | 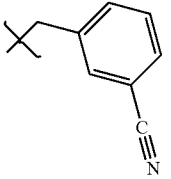 | 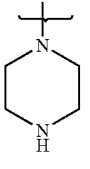 | 4-Methyl-2-[[5,6,7,8-tetrahydro-7-((3-(cyano)phenyl)methyl)-4-(1-piperazinyl)pyrido[3,4-d]pyrimidin-2-yl]amino]-5-thiazolecarboxylic acid ethyl ester | 1.87 | 519.16 |
| C10 | 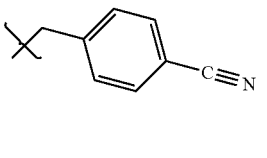 | 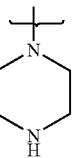 | 4-Methyl-2-[[5,6,7,8-tetrahydro-7-((4-(cyano)phenyl)methyl)-4-(1-piperazinyl)pyrido[3,4-d]pyrimidin-2-yl]amino]-5-thiazolecarboxylic acid ethyl ester | 1.91 | 519.35 |
| C11 | 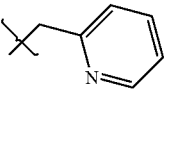 | 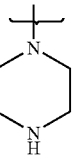 | 4-Methyl-2-[[5,6,7,8-tetrahydro-7-((2-pyridyl)methyl)-4-(1-piperazinyl)pyrido[3,4-d]pyrimidin-2-yl]amino]-5-thiazolecarboxylic acid ethyl ester | 1.49 | 495.19 |
| C12 | 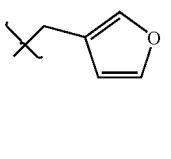 | 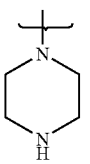 | 4-Methyl-2-[[5,6,7,8-tetrahydro-7-((3-furanyl)methyl)-4-(1-piperazinyl)pyrido[3,4-d]pyrimidin-2-yl]amino]-5-thiazolecarboxylic acid ethyl ester | 1.67 | 484.21 |

TABLE C2-continued

| Ex. | R⁵ | Z | Name | HPLC Retention (min) | MS Reported |
|---|---|---|---|---|---|
| C13 | 3-thienylmethyl | piperazinyl | 4-Methyl-2-[[5,6,7,8-tetrahydro-7-((3-thenyl)methyl)-4-(1-piperazinyl)pyrido[3,4-d]pyrimidin-2-yl]amino]-5-thiazolecarboxylic acid ethyl ester | 1.84 | 500.17 |
| C14 | 4-pyridylmethyl | piperazinyl | 4-Methyl-2-[[5,6,7,8-tetrahydro-7-((4-pyridyl)methyl)-4-(1-piperazinyl)pyrido[3,4-d]pyrimidin-2-yl]amino]-5-thiazolecarboxylic acid ethyl ester | 1.34 | 495.19 |
| C15 | 2-cyanophenylmethyl | piperazinyl | 4-Methyl-2-[[5,6,7,8-tetrahydro-7-((2-(cyano)phenyl)methyl)-4-(1-piperazinyl)pyrido[3,4-d]pyrimidin-2-yl]amino]-5-thiazolecarboxylic acid ethyl ester | 2.13 | 519.23 |
| C16 | 2-thiazolylmethyl | piperazinyl | 4-Methyl-2-[[5,6,7,8-tetrahydro-7-((2-thiazolyl)methyl)-4-(1-piperazinyl)pyrido[3,4-d]pyrimidin-2-yl]amino]-5-thiazolecarboxylic acid ethyl ester | 1.84 | 501.49 |
| C17 | 4-fluorophenylmethyl | piperazinyl | 4-Methyl-2-[[5,6,7,8-tetrahydro-7-((4-fluorophenyl)methyl)-4-(1-piperazinyl)pyrido[3,4-d]pyrimidin-2-yl]amino]-5-thiazolecarboxylic acid ethyl ester | 1.98 | 512.33 |
| C18 | 2-thenylmethyl | piperazinyl | 4-Methyl-2-[[5,6,7,8-tetrahydro-7-((2-thenyl)methyl)-4-(1-piperazinyl)pyrido[3,4-d]pyrimidin-2-yl]amino]-5-thiazolecarboxylic acid ethyl ester | 1.88 | 500.31 |
| C19 | 1-(3-pyridyl)ethyl | piperazinyl | 4-Methyl-2-[[5,6,7,8-tetrahydro-7-(1-(3-pyridyl)ethyl)-4-(1-piperazinyl)pyrido[3,4-d]pyrimidin-2-yl]amino]-5-thiazolecarboxylic acid ethyl ester | 1.41 | 509.48 |
| C20 | 1-(2-pyridyl)ethyl | piperazinyl | 4-Methyl-2-[[5,6,7,8-tetrahydro-7-(1-(2-pyridyl)ethyl)-4-(1-piperazinyl)pyrido[3,4-d]pyrimidin-2-yl]amino]-5-thiazolecarboxylic acid ethyl ester | 1.64 | 509.18 |
| C21 | phenylmethyl | 3-oxo-1-piperazinyl | 4-Methyl-2-[[5,6,7,8-tetrahydro-7-(phenyl)methyl)-4-(3-oxo-1-piperazinyl)pyrido[3,4-d]pyrimidin-2-yl]amino]-5-thiazolecarboxylic acid ethyl ester | 2.28 | 508.35 |

TABLE C2-continued

| Ex. | R⁵ | Z | Name | HPLC Retention (min) | MS Reported |
|---|---|---|---|---|---|
| C22 | | | 4-Methyl-2-[[5,6,7,8-tetrahydro-7-((tetrahydrofuran-3-yl)oxycarbonyl)-4-[4-(aminosulfonyl)phenyl]methyl]-amino]pyrido[3,4-d]pyrimidin-2-yl]amino]-5-thiazolecarboxylic acid ethyl ester | 1.40 | 618.47 |
| C23 | | —OBu | 4-Methyl-2-[[5,6,7,8-tetrahydro-7-((tetrahydrofuran-3-yl)oxycarbonyl)-4-(butyloxy)pyrido[3,4-d]pyrimidin-2-yl]amino]-5-thiazolecarboxylic acid ethyl ester | 2.02 | 506.51 |
| C24 | | | 4-Methyl-2-[[5,6,7,8-tetrahydro-7-(dimethylaminosulfonyl)-4-((4-hydroxy)-1-piperidinyl)pyrido[3,4-d]pyrimidin-2-yl]amino]-5-thiazolecarboxylic acid ethyl ester | 2.34 | 526.23 |

We claim:

1. A compound of Formula (I)

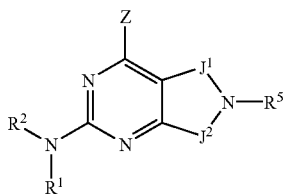

including enantiomers, diastereomers, and pharmaceutically acceptable salts thereof, wherein:

$R^1$ is hydrogen or alkyl;

$R^2$ is
- (a) thiazolyl optionally substituted with one to three groups $T^1$, $T^2$, and/or $T^3$, where $T^1$, $T^2$, $T^3$ are independently H, alkyl, haloalkyl, halo, heteroaryl, $C(O)_tT^6$, $OT^6$ or $-T^4NT^7T^8$;
- (b) phenyl substituted at the para position with $T^1$, and optionally further substituted with groups $T^2$ and $T^3$ where
  - $T^1$ is optionally substituted heteroaryl, cyano, $C(O)_tT^6$, or $S(O)_tN(T^9)T^6$, and
  - $T^2$ and $T^3$ are independently H, heteroaryl, cyano, $C(O)_tT^6$, $S(O)_tN(T^9)T^6$, halo alkyl, or haloalkyl; or
- (c) tetrahydroindole, quinol-6-yl, quinazolin-7-yl, cinnolin-6-yl, isoquinol-6-yl, or phthalazin-6-yl, any of which may be optionally substituted with one to three groups $T^1$, $T^2$ and/or $T^3$;

Z is $-NR^3R^4$;

$R^3$ is H, alkyl or cycloalkyl;

$R^4$ is (aryl)alkyl optionally independently substituted with one to three groups $T^{1a}$, $T^{2a}$, and/or $T^{3a}$, where $T^{1a}$, $T^{2a}$ and/or $T^{3a}$ are independently $OT^6$, $S(O)_tT^6$, or $S(O)_tN(T^9)T^6$;

or $R^3$ and $R^4$ may be taken together with the nitrogen atom to which they are attached to form piperidyl, piperazinyl, or morpholinyl, any of which may be optionally independently substituted with one to three groups $T^{1a}$, $T^{2a}$, and/or $T^{3a}$ where $T^{1a}$, $T^{2a}$ and/or $T^{3a}$ are independently H, hydroxy, oxo, or $-C(O)_tT^6$;

$R^5$ is
- (a) hydrogen or cyano;
- (b) alkyl, alkenyl, (cycloalkyl)alkyl, (aryl)alkyl, or (heteroaryl)alkyl any of which may be optionally independently substituted one to three groups $T^{1b}$, $T^{2b}$, and/or $T^{3b}$ wherein $T^{1b}$, $T^{2b}$ and/or $T^{3b}$ are independently H, cyano, $-OT^6$, or $-S(O)_tT^6$; or
- (c) $-C(O)R^6$, $-C(O)OR^6$, $-C(O)-C(O)OR^6$, or $-SO_2R^{6a}$;

$R^6$ is H, alkyl, alkenyl, $-NR^{3b}R^{4b}$, heterocyclo, (heterocyclo)alkyl, (hydroxy)alkyl, (alkoxy)alkyl, (aryloxy)alkyl or $(NR^{3b}R^{4b})$alkyl, any of which may be optionally independently substituted one to three groups $T^{1b}$, $T^{2b}$ and/or $T^{3b}$ where $T^{1b}$, $T^{2b}$ and/or $T^{3b}$ are independently H, alkyl, $-C(O)_tH$, $-C(O)_tT^6$, $-OC(O)T^6$, $-OH$, $-OT^6$, or $-S(O)_tT^6$;

$R^{6a}$ is H, alkyl, alkenyl, $-NR^{3b}R^{4b}$, heterocyclo, (heterocyclo)alkyl, (hydroxy)alkyl, (alkoxy)alkyl, (aryloxy)alkyl, or (NR$^{3b}$R$^{4b}$)alkyl, any of which may be optionally independently substituted with one to three groups T$^{1b}$, T$^{2b}$, and/or T$^{3b}$ where T$^{1b}$, T$^{2b}$, and/or T$^{3b}$ are independently H, alkyl, —C(O)$_t$H, —C(O)$_t$T$^6$, —OC(O)T$^6$, —OH, —OT$^6$ or —S(O)$_t$T$^6$;

J$^1$ and J$^2$ are independently optionally substituted C$_{1-3}$ alkylene, provided that J$^1$ and J$^2$ are not both greater than C$_2$ alkylene; and T$^{1-1b}$, T$^{2-2b}$, and T$^{3-3b}$ are each independently
(1) hydrogen or T$^6$, where T$^6$ is
   (i) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl or (heteroaryl)alkyl;
   (ii) a group (i) which is itself substituted by one or more of the same or different groups (i); or
   (iii) a group (i) or (ii) which is independently substituted by one or more of the following groups (2) to (13) of the definition of T$^{1-1b}$, T$^{2-2b}$, and T$^{3-3b}$,
(2) —OH or —OT$^6$;
(3) —SH or —ST$^6$;
(4) —C(O)$_t$H, —C(O)$_t$T$^6$ or —O—C(O)T$^6$, wherein t is 1 or 2;
(5) —SO$_3$H, —S(O)$_t$T$^6$ or S(O)$_t$N(T$^9$)T$^6$;
(6) halo;
(7) cyano;
(8) nitro;
(9) -T$^4$-NT$^7$T$^8$;
(10) -T$^4$-N(T$^9$)-T$^5$-NT$^7$T$^8$;
(11) -T$^4$-N(T$^{10}$)-T$^5$-T$^6$;
(12) -T$^4$-N(T$^{10}$)-T$^5$-H; or
(13) oxo;

T$_4$ T$^5$ are each independently
(1) a single bond;
(2) -T$^{11}$-S(O)$_t$-T$^{12}$-;
(3) -T$^{11}$-C(O)-T$^{12}$-;
(4) -T$^{11}$-C(S)-T$^{12}$-;
(5) -T$^{11}$-O-T$^{12}$-;
(6) -T$^{11}$-S-T$^{12}$-;
(7) -T$^{11}$-O—C(O)-T$^{12}$-;
(8) -T$^{11}$-C(O)—O-T$^{12}$-;
(9) -T$^{11}$-C(=NT$^{9a}$)-T$^{12}$-; or
(10) -T$^{11}$-C(O)—C(O)-T$^{12}$-;

T$^7$,T$^8$,T$^9$,T$^{9a}$, and T$^{10}$
(1) are each independently hydrogen or a group provided in the definition of T$^6$, or
(2) T$^7$ and T$^8$ may together be alkylene or alkenylene, completing a 3- to 8-membered saturated or unsaturated ring together with the atoms to which they are attached, which ring is unsubstituted or substituted with one or more groups listed in the description of T$^{1-1b}$, T$^{2-2b}$, and/or T$^{3-3b}$; or
(3) T$^7$ or T$^8$, together with T$^9$, may be alkylene or alkenylene completing a 3- to 8-membered saturated or unsaturated ring together with the nitrogen atoms to which they are attached, which ring is unsubstituted or substituted with one or more groups listed in the description of T$^{1-1b}$, T$^{2-2b}$, and/or T$^{3-3b}$; or
(4) T$^7$ and T$^8$ or T$^9$ and T$^{10}$ together with the nitrogen atom to which they are attached may combine to form a group —N=CT$^{13}$T$^{14}$ where T$^{13}$ and T$^{14}$ are each independently H or a group provided in the definition of T$^6$; and T$^{11}$ and T$^{12}$ are each independently
(1) a single bond;
(2) alkylene;
(3) alkenylene; or
(4) alkynylene.

2. A compound of claim 1 having formula (IIa) or (IIb)

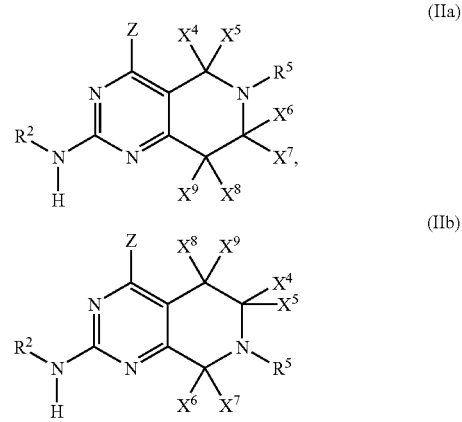

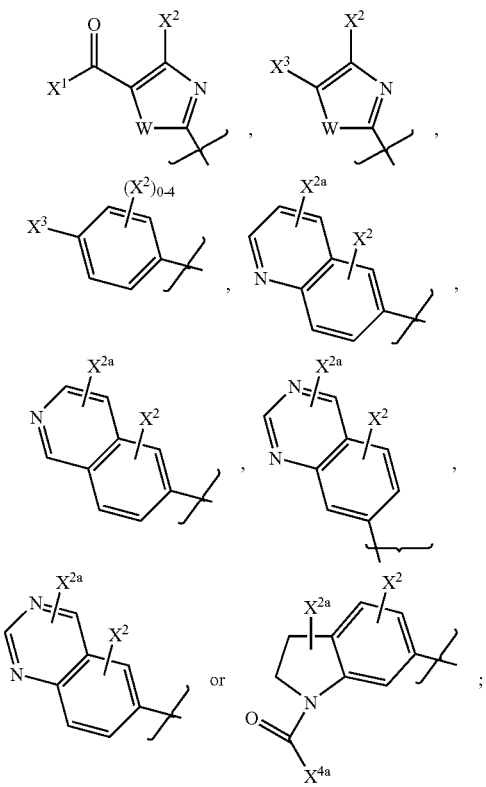

including enantiomers, diastereomers, and pharmaceutically acceptable salts thereof, wherein:

R$^2$ is

W is O or S;
X$^1$ is NHT$^8$ or OT$^6$;
X$^2$ and X$^{2a}$ are independently hydrogen, halo, OT$^6$, alkyl, or haloalkyl;
X$^3$ is optionally substituted heteroaryl cyano, C(O)$_t$T$^6$, or S(O)$_t$NT$^7$T$^8$;
X$^{4a}$ is alkyl, haloalkyl, NHT$^8$, or OT$^6$;
X$^4$, X$^5$, X$^6$ and X$^7$ are independently chosen from hydrogen, T$^6$, OT$^6$, or NT$^7$T$^8$; and/or X$^4$ and X$^5$ may be taken together to be a carbonyl group; and/or X$^6$ and X$^7$ may be taken together to be a carbonyl group; and $X^8$ and $X^9$ are independently hydrogen, $T^6$, $OT^6$, or $NT^7T^8$.

3. A compound of claim 1 having formula (IIIa), (IIIb) or (IIIc)

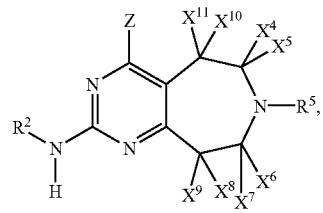
(IIIa)

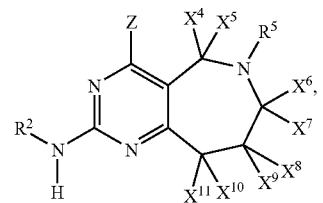
(IIIb)

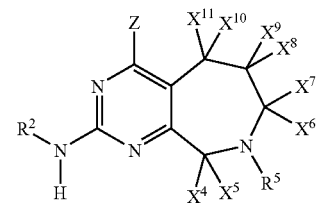
(IIIc)

including enantiomers, diastereomers, and pharmaceutically acceptable salts thereof, wherein:

R is

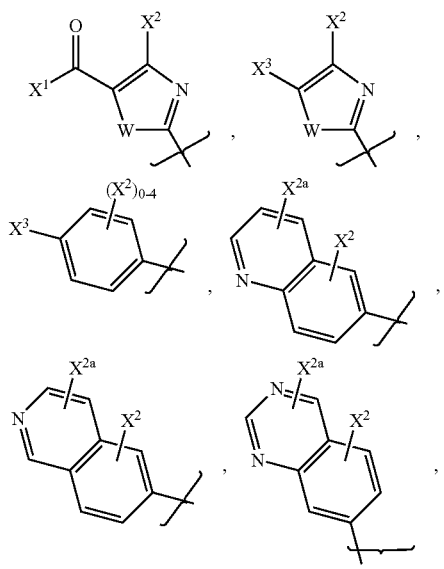

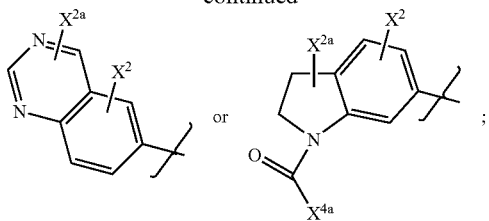

W is O or S;

$X^1$ is $NHT^8$ or $OT^6$;

$X^2$ and $X^{2a}$ are independently hydrogen, halo, $OT^6$, alkyl, or haloalkyl;

$X^3$ is optionally substituted heteroaryl cyano, $C(O)_tT^6$, or $S(O)_tNT^7T^8$;

$X^{4a}$ is alkyl, haloalkyl, $NHT^8$, or $OT^6$;

$X^4$, $X^5$, $X^6$ and $X^7$ are independently hydrogen, $T^6$, $OT^6$ or $NT^7T^8$; or $X^4$ and $X^5$ may be taken together to be a carbonyl group; or $X^6$ and $X^7$ may be taken together to be a carbonyl group; and $X^8$, $X^9$, $X^{10}$ and $X^{11}$ are independently hydrogen, $T^6$, $OT^6$, or $NT^7T^8$.

4. A compound of claim 1 having formula (IV)

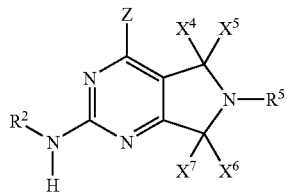
(IV)

including enantiomers, diastereomers, and pharmaceutically acceptable salts thereof, wherein:

$R^2$ is

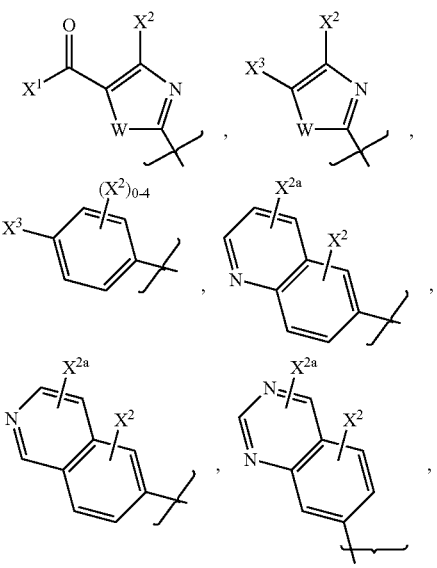

-continued

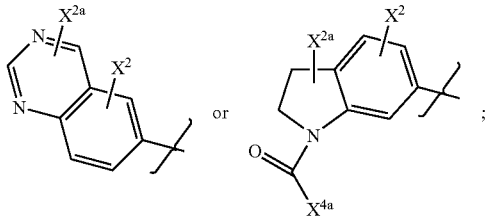

W is O or S;
$X^1$ is $NHT^8$ or $OT^6$;
$X^2$ and $X^{2a}$ are independently hydrogen, halo, $OT^6$, alkyl, or haloalkyl;
$X^3$ is optionally substituted heteroaryl, cyano, $C(O)_tT^6$, or $S(O)_tNT^7T^8$;
$X^{4a}$ is alkyl, haloalkyl, $NHT^8$, or $OT^6$;
$X^4$, $X^5$, $X^6$ and $X^7$ are independently hydrogen, $T^6$, $OT^6$, or $NT^7T^8$; or $X^4$ and $X^5$ may be taken together to be a carbonyl group; or $X^6$ and $X^7$ may be taken together to be a carbonyl group.

5. A compound selected from the following:
(i)
- '2-[[4-[[[4-(Methylsulfonyl)phenyl]methyl]amino]-5,6,7,8-tetrahydro-6-methylpyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(phenylmethyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydropyrido[4,3-d]pyrimidin-2-yl]amino]-4-methyl-5-thiazolecarboxylic acid ethyl ester;
- 2-[[6-[(Acetyloxy)acetyl]-4-[[[4-(aminosulfonyl)phenyl]methyl]amino]-5,6,7,8-tetrahydropyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(hydroxyacetyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(ethoxycarbonyl)pyrido[4,3-d]pyrimidin-2-yl]amino]-4-methyl-5-thiazolecarboxylic acid ethyl ester,
- 2-[[4-[[[3,4,5-Trimethoxyphenyl]methyl]amino]-5,6,7,8-tetrahydro-6-(formyl)pyrido[4,3-d]pyrimidin-2-yl]amino]-4-methyl-5-thiazolecarboxylic acid ethyl ester,
- 2-[[4-[[[3,4,5-Trimethoxyphenyl]methyl]amino]-5,6,7,8-tetrahydro-6-(morpholin-4-ylmethylcarbonyl)pyrido[4,3-d]pyrimidin-2-yl]amino]-4-methyl-5-thiazolecarboxylic acid ethyl ester,
- 2-[[4-[[[3,4,5-Trimethoxyphenyl]methyl]amino]-5,6,7,8-tetrahydro-6-(4-methylpiperazin-1-ylmethylcarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-((2-ethoxy) ethoxycarbonyl)pyrido[4,3-d]pyrimidin-2-yl]amino]-4-methyl-5-thiazolecarboxylic acid ethyl ester,
- 2-[[4-[[[4-(Methylsulfonyl)phenyl]methyl]amino]-5,6,7,8-tetrahydro-6-((2-ethoxy) ethoxycarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(cyano)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(allyloxycarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(allyloxycarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(phenyloxycarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(methoxycarbonylcarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(dimethylaminomethylcarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(carboxyethylcarbonyl)pyrido[4,3-d]pyrimidin-2-yl]amino]-4-methyl-5-thiazolecarboxylic acid ethyl ester,
- 2-[[4-[[[3,4,5-Trimethoxyphenyl]methyl]amino]-5,6,7,8-tetrahydro-6-(cyclopropylmethyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-((3-(tetrahydrofuranyl)oxycarbonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-(cyclopropylmethyl)pyrido[4,3-d]pyrimidin-2-yl]amino]-4-methyl-5-thiazolecarboxylic acid ethyl ester,
- 2-[[4-[[[3,4,5-Trimethoxyphenyl]methyl]amino]-5,6,7,8-tetrahydro-6-(hydroxyacetyl)pyrido[4,3-d]pyrimidin-2-yl]amino]-4-methyl-5-thiazolecarboxylic acid ethyl ester,
- 2-[[4-[[[3,4,-Dimethoxyphenyl]methyl]amino]-5,6,7,8-tetrahydro-6-(2-propenyl)pyrido[4,3-d]pyrimidin-2-yl]amino]-4-methyl-5-thiazolecarboxylic acid ethyl ester,
- 2-[[4-[[[3,4,5-Trimethoxyphenyl]methyl]amino]-5,6,7,8-tetrahydro-6-(methylsulfonyl)pyrido[4,3-d]pyrimidin-2-yl]amino]-4-methyl-5-thiazolecarboxylic acid ethyl ester,
- 2-[[4-[[[4-(Aminosulfonyl)phenyl]methyl]amino]-5,6,7,8-tetrahydro-6-methylpyrido[4,3-d]pyrimidin-2-yl]amino]-4-methyl-5-thiazolecarboxylic acid ethyl ester,
- 6-[[4-morpholinyl-5,6,7,8-tetrahydro-6-(phenylmethyl)pyrido[4,3-d]pyrimidin-2-yl]amino]-quinoline,
- 1-[[4-[[[4-(Aminosulfonyl)phenyl]methyl]amino]-5,6,7,8-tetrahydro-6-(phenylmethyl)pyrido[4,3-d]pyrimidin-2-yl]amino]-4-[(1-methyl)imidazol-5yl]benzene,
- 2-[[4-[[[4-(Methylsulfonyl)phenyl]methyl]amino]-5,6,7,8-tetrahydro-6-(ethoxycarbonyl)pyrido[4,3-d]pyrimidin-2-yl]amino]-4-methyl-5-thiazolecarboxylic acid methyl amide,
- Aminosulfonyl)phenyl]methyl]amino]-6,7,8,9-tetrahydro-5H-pyrimido[4,5-d]azepin-2-yl]amino]-4-methyl-5-thiazolecarboxylic acid ethyl ester, 4-Methyl-2-[[6,7,8,9-tetrahydro-7-(hydroxyacetyl)-4-[[[4-(methylsulfonyl)phenyl]methyl]amino]-5H-pyrimido[4,5-d]azepin-2-yl]amino]-5-thiazolecarboxylic acid ethyl ester, 4-Methyl-2-[[6,7,8,9-tetrahydro-4-[[[4-(methylsulfonyl)phenyl]methyl]amino]-7-(4-morpholinylacetyl)-5H-pyrimido[4,5-d]azepin-2-yl]amino]-5-thiazolecarboxylic acid ethyl ester, 2-[[7-[(Acetyloxy)acetyl]-6,7,8,9-tetrahydro-4-[[[4-(methylsulfonyl)phenyl]methyl]amino]-5H-pyrimido[4,5-d]azepin-2-yl]amino]-4-methyl-5-thiazolecarboxylic acid ethyl ester, 4-Methyl-2-[[5,6,7,8-tetrahydro-7-(phenylmethyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-(phenylmethyl)-4-[4-(methylsulfonyl)phenyl]methyl]amino]pyrido[3,4-d]pyrimidin-2-yl]amino]-5-thiazolecarboxylic acid ethyl ester, 4-Methyl-2-[[5,6,7,8-tetrahydro-7-(phenylmethyl)-4-[4-(aminosulfonyl)phenyl]methyl]amino]pyrido[3,4-d]pyrimidin-2-yl]amino]-5-thiazolecarboxylic acid ethyl ester, 4-Methyl-2-[[5,6,7,8-tetrahydro-7-((3,4-(dimethoxy)phenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((3,4,5-(trimethoxy)phenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((4-(methylsulfonyl)phenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((3-pyridyl)methyl)-4-(1-piperazinyl)pyrido[3,4-d]pyrimid-2-yl]amino]-5-thiazolecarboxylic acid ethyl ester, 4-Methyl-2-[[5,6,7,8-tetrahydro-7-((2-furanyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((3-(cyano)phenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((4-(cyano)phenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((2-pyridyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((3-furanyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((3-thenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((4-pyridyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((2-(cyano)phenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((2-thiazolyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((4-fluorophenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-((2-thenyl)methyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-(1-(3-pyridyl)ethyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-(1-(2-pyridyl)ethyl)-4-(1-piperazinyl)pyrido[3,4-d]pyrimidin-2-yl]amino]-5-thiazolecarboxylic acid ethyl ester, 4-Methyl-2-[[5,6,7,8-tetrahydro-7-(phenyl)methyl)-4-(3-oxo- 1-piperazinyl)pyndo[3,4-d]pyrimidin-2-yl]amino]-5-thiazolecarboxylic acid ethyl ester, 4-Methyl-2-[[5,6,7,8-tetrahydro-7-((tetrahydrofuran-3-yl)oxycarbonyl)-4-[4-(aminosulfonyl)phenyl]methyl]amino]pyrido[3,4-d]pyrimidin-2-yl]amino]-5-thiazolecarboxylic acid ethyl ester, 4-Methyl-2-[[5,6,7,8-tetrahydro-7-((tetrahydrofuran-3-yl)oxycarbonyl)-4-(butyloxy)pyrido[3,4-d]pyrimidin-2-yl]amino]-5-thiazolecarboxylic acid ethyl ester, and 4-Methyl-2-[[5,6,7,8-tetrahydro-7-(dimethylaminosulfonyl)-4-((4-hydroxy)-1-piperidinyl)pyrido[3,4-d]pyrimidin-2-yl]amino]-5-thiazolecarboxylic acid ethyl ester; or (ii) an enantiomer, diastereomer, or a pharmaceutically acceptable salt of (i), thereof.

6. A compound according to claim 5, including enantiomers, diastereomers, and pharmaceutically acceptable salts, thereof, selected from the following:

(i)

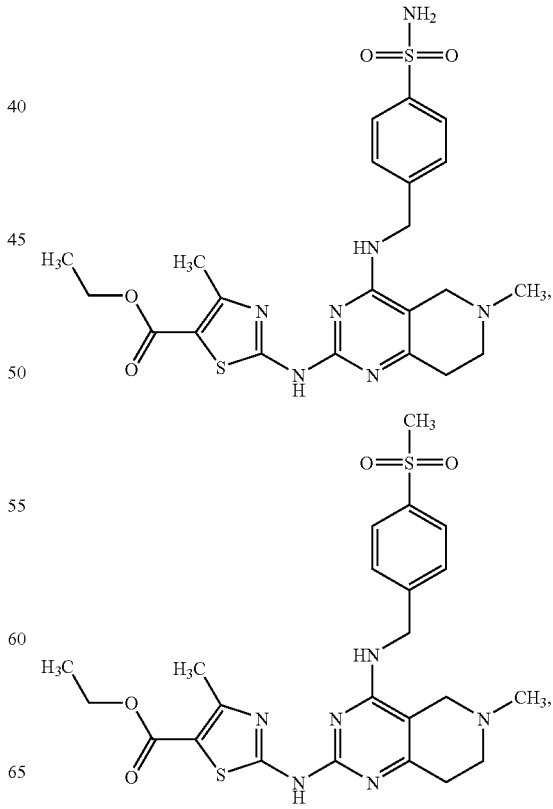

-continued
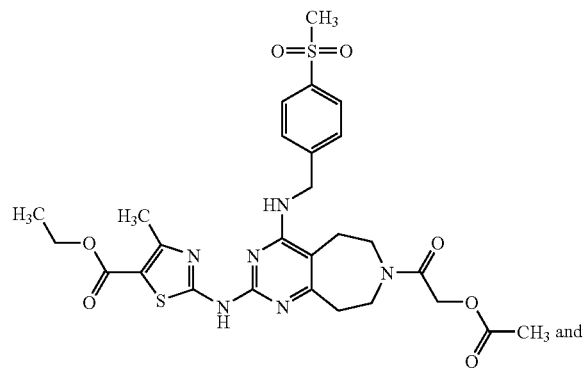
and
-continued
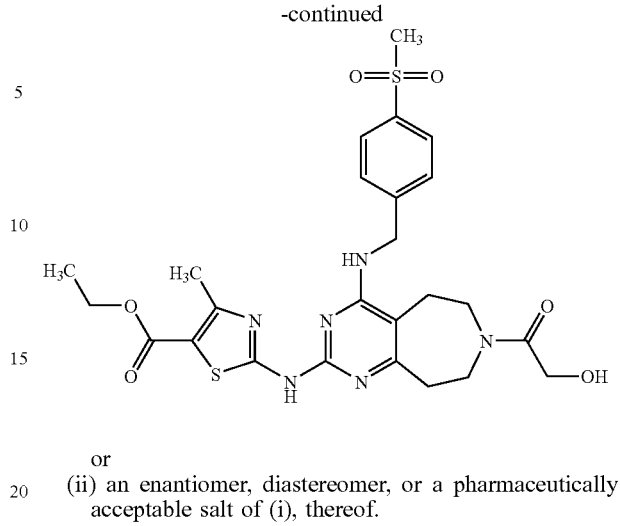
or
(ii) an enantiomer, diastereomer, or a pharmaceutically acceptable salt of (i), thereof.
* * * * *